United States Patent
Puech et al.

(10) Patent No.: US 8,455,491 B2
(45) Date of Patent: Jun. 4, 2013

(54) 6-CYCLOAMINO-3-(PYRIDAZIN-4-YL) IMIDAZO[1,2-B]PYRIDAZINE AND DERIVATIVES AND PHARMACEUTICAL COMPOSITIONS COMPRISING THE SAME

(75) Inventors: Frederic Puech, Paris (FR); Yulin Chiang, Bridgewater, NJ (US); Sylvain Cote Des Combes, Paris (FR); Adrien Tak Li, Bridgewater, NJ (US); Philippe Burnier, Paris (FR)

(73) Assignee: Sanofi, Paris (FR)

( * ) Notice: Subject to any disclaimer, the term of this patent is extended or adjusted under 35 U.S.C. 154(b) by 18 days.

(21) Appl. No.: 12/685,030

(22) Filed: Jan. 11, 2010

(65) Prior Publication Data
US 2010/0152157 A1 Jun. 17, 2010

Related U.S. Application Data

(63) Continuation of application No. PCT/FR2008/001057, filed on Jul. 18, 2008.

(60) Provisional application No. 60/950,711, filed on Jul. 19, 2007.

(30) Foreign Application Priority Data

Jul. 19, 2007 (FR) ................................ 07 05224

(51) Int. Cl.
*C07D 487/04* (2006.01)
*A61K 31/00* (2006.01)

(52) U.S. Cl.
USPC ......................................... 514/248; 544/236

(58) Field of Classification Search
USPC .......................................... 544/236; 514/248
See application file for complete search history.

(56) References Cited

U.S. PATENT DOCUMENTS
7,402,672 B2 7/2008 Metz et al.

FOREIGN PATENT DOCUMENTS

| WO | WO 89/01333 | 2/1989 |
|---|---|---|
| WO | WO 2005/080355 | 9/2005 |
| WO | WO 2007/009773 | 1/2007 |
| WO | WO 2007/013673 | 2/2007 |
| WO | WO 2007/025540 | 3/2007 |

*Primary Examiner* — Susanna Moore
*Assistant Examiner* — Cecilia M Jaisle
(74) *Attorney, Agent, or Firm* — Scully, Scott, Murphy & Presser, P.C.

(57) ABSTRACT

The invention relates to the 6-cycloamino-3-(pyridazin-4-yl) imidazo[1,2-b]pyridazine derivatives corresponding to general formula (I):

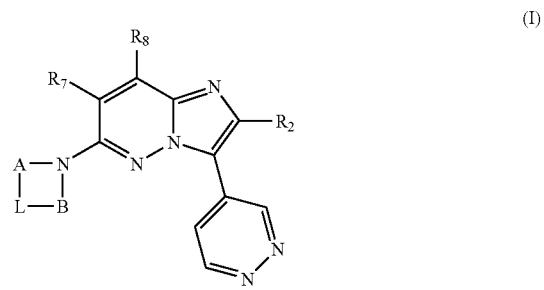

Wherein $R_2$, $R_7$, $R_8$, A, L and B are as defined herein. Also disclosed are the preparative methods and therapeutic use thereof.

15 Claims, No Drawings

6-CYCLOAMINO-3-(PYRIDAZIN-4-YL) IMIDAZO[1,2-B]PYRIDAZINE AND DERIVATIVES AND PHARMACEUTICAL COMPOSITIONS COMPRISING THE SAME

This application is a continuation of International application No. PCT/FR2008/001,057, filed Jul. 18, 2008, which is incorporated herein by reference in its entirety; which claims the benefit of U.S. Provisional Application No. 60/950,711, filed Jul. 19, 2007 and claims the benefit of priority of French patent application Ser. No. 07/05,224, filed Jul. 19, 2007.

The present invention relates to 6-cycloamino-3-(pyridazin-4-yl)imidazo[1,2-b]pyridazine derivatives, to a process for preparing them and to their therapeutic use, in the treatment or prevention of diseases involving casein kinase 1 epsilon and/or casein kinase 1 delta.

One subject of the present invention is compounds corresponding to the general formula (I)

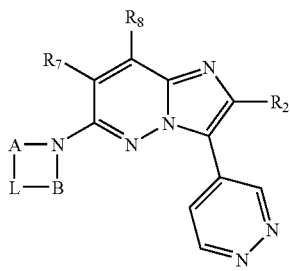

in which:
- $R_2$ represents an aryl group optionally substituted with one or more substituents chosen from halogen atoms and the groups $C_{1-6}$ alkyl, $C_{1-6}$alkyloxy, $C_{1-6}$alkylthio, $C_{1-6}$-fluoroalkyl, $C_{1-6}$-fluoroalkyloxy and —CN;
- A represents a group $C_{1-7}$-alkylene optionally substituted with one or two groups $R_a$;
- B represents a group $C_{1-7}$-alkylene optionally substituted with a group $R_b$;
- L represents either a nitrogen atom optionally substituted with a group $R_c$ or $R_d$, or a carbon atom substituted with a group $R_{e1}$ and a group $R_d$ or two groups $R_{e2}$;

the carbon atoms of A and B being optionally substituted with one or more groups $R_f$, which may be identical to or different from one another;

$R_a$, $R_b$ and $R_c$ are defined such that:
- two groups $R_a$ may together form a group $C_{1-6}$-alkylene;
- $R_a$ and $R_b$ may together form a bond or a group $C_{1-6}$-alkylene;
- $R_a$ and $R_c$ may together form a bond or a group $C_{1-6}$-alkylene;
- $R_b$ and $R_c$ may together form a bond or a group $C_{1-6}$-alkylene;

$R_d$ represents a group chosen from a hydrogen atom and the groups $C_{1-6}$-alkyl, $C_{3-7}$-cycloalkyl, $C_{3-7}$-cycloalkyl-$C_{1-6}$-alkyl, hydroxy-$C_{1-6}$-alkyl, $C_{1-6}$-alkyloxy-$C_{1-6}$-alkyl, $C_{1-6}$-alkylthio-$C_{1-6}$-alkyl, $C_{1-6}$-fluoroalkyl and benzyl;

$R_{e1}$ represents a group —$NR_4R_5$ or a cyclic monoamine optionally comprising an oxygen atom, the cyclic monoamine being optionally substituted with one or more substituents chosen from a fluorine atom and the groups $C_{1-6}$-alkyl, $C_{1-6}$-alkyloxy and hydroxyl;

Two groups $R_{e2}$ form, with the carbon atom that bears them, a cyclic monoamine optionally comprising an oxygen atom, this cyclic monoamine being optionally substituted with one or more groups $R_f$, which may be identical to or different from one another;

$R_f$ represents a group $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl or benzyl;

$R_4$ and $R_5$ represent, independently of each other, a hydrogen atom or a group $C_{1-6}$-alkyl, $C_{3-7}$-cycloalkyl or $C_{3-7}$-cycloalkyl-$C_{1-6}$-alkyl;

$R_7$ and $R_8$ represent, independently of each other, a hydrogen atom or a group $C_{1-6}$-alkyl.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or addition salts with acids. Such addition salts form part of the invention. The salts are advantageously prepared with pharmaceutically acceptable acids, but the salts of other acids that are useful, for example, for purifying and isolating compounds of formula (I) also form part of the invention.

The compounds of formula (I) may also exist in the form of hydrates or solvates, i.e. in the form of associations or combinations with one or more molecules of water or with a solvent. Such hydrates and solvates also form part of the invention.

In the context of the invention, the following definitions apply:

$C_{t-z}$ in which t and z may take values from 1 to 7, a carbon-based chain possibly containing from t to z carbon atoms, for example $C_{1-7}$ is a carbon-based chain that may contain from 1 to 7 carbon atoms;

alkyl, a linear or branched, saturated aliphatic group; for example, a group $C_{1-7}$-alkyl represents a linear or branched carbon-based chain of 1 to 7 carbon atoms, for example a methyl, ethyl, propyl, isopropyl, butyl, isobutyl, tert-butyl, pentyl, hexyl or heptyl;

alkylene, a linear or branched, saturated divalent alkyl group, for example a group $C_{1-6}$-alkylene represents a linear or branched divalent carbon-based chain of 1 to 6 carbon atoms, for example a methylene, ethylene, 1-methylethylene or propylene;

cycloalkyl, a cyclic alkyl group, for example a group $C_{3-7}$-cycloalkyl represents a cyclic carbon-based group of 3 to 7 carbon atoms, for example a cyclopropyl, cyclobutyl, cyclopentyl, cyclohexyl or cycloheptyl;

hydroxyl, a group —OH;

—CN, a nitrile group;

cyclic monoamine, a saturated cyclic or polycyclic carbon-based chain, optionally bridged or condensed, comprising one nitrogen atom;

By way of example of a compound formed by N, A, L and B constituting a cyclic monoamine optionally comprising an oxygen atom, mention may in particular be made of aziridine, azetidine, pyrrolidine, piperidine, azepine, morpholine, homopiperidine, decahydroquinoline, decahydroisoquinoline, azabicycloheptane, azabicyclooctane, azabicyclononane, azaoxobicycloheptane and azaoxobicyclooctane;

cyclic diamine, a saturated cyclic or polycyclic carbon-based chain, optionally bridged or condensed, comprising 2 nitrogen atoms;

By way of example of a compound formed by N, A, L and B constituting a cyclic diamine optionally comprising an oxygen atom, mention may in particular be made of piperazine, homopiperazine, diazacyclooctane, diazacyclononane, diazacyclodecane, diazacycloundecane, octahydropyrrolopyrazine, octahydropyrrolodiazepine, octahydropyrrolopyrrole, octahydropyrrolopyridine, decahydronaphthyridine, diazabicycloheptane, diazabicyclooctane, diazabicyclononane, diazaspiroheptane, diazaspirooctane, diazaspirononane, diazaspirodecane, diazaspiroundecane and oxadiazaspiroundecane;

hydroxyalkyl, an alkyl group in which one hydrogen atom has been substituted with a hydroxyl group;

alkyloxy, a group —O-alkyl;

alkylthio, a group —S-alkyl;

fluoroalkyl, an alkyl group in which one or more hydrogen atoms have been substituted with a fluorine atom;

fluoroalkyloxy, an alkyloxy group in which one or more hydrogen atoms have been substituted with a fluorine atom;

a halogen atom, a fluorine, chlorine, bromine or iodine atom;

aryl, a monocyclic or bicyclic aromatic group containing between 6 and 10 carbon atoms. By way of example of an aryl group, mention may be made of phenyl or naphthyl groups.

Among the compounds of general formula (I) that are subjects of the invention, a first group of compounds is constituted by the compounds for which $R_2$ represents a phenyl optionally substituted with one or more halogen atoms or groups $C_{1-6}$ alkyl or $C_{1-6}$-fluoroalkyl;

A, L, B, $R_7$ and $R_8$ being as defined above.

Among the compounds of general formula (I) that are subjects of the invention, a second group of compounds is constituted by the compounds for which $R_2$ represents a phenyl optionally substituted with one or more fluorine or chlorine atoms or methyl or trifluoromethyl groups;

A, L, B, $R_7$ and $R_8$ being as defined above.

Among the compounds of general formula (I) that are subjects of the invention, a third group of compounds is constituted by the compounds for which $R_2$ represents a phenyl, 3-fluorophenyl, 4-fluorophenyl, 3,4-difluorophenyl, 3,5-difluorophenyl, 3,5-dichlorophenyl, 3,5-dimethylphenyl, or 3,5-di(trifluoromethyl)phenyl;

A, L, B, $R_7$ and $R_8$ being as defined above.

Among the compounds of general formula (I) that are subjects of the invention, a fourth group of compounds is constituted by the compounds for which $R_7$ and $R_8$ represent, independently of each other, a hydrogen atom or a methyl group;

$R_2$, A, L and B being as defined above.

Among the compounds of general formula (I) that are subjects of the invention, a fifth group of compounds is constituted by the compounds for which:

A represents a group $C_{1-7}$-alkylene optionally substituted with one or two groups $R_a$, B represents a group $C_{1-7}$-alkylene optionally substituted with a group $R_b$;

L represents a nitrogen atom optionally substituted with a group $R_c$ or $R_d$;

the carbon atoms of A and of B being optionally substituted with one or more groups $R_f$, which may be identical to or different from each other;

$R_a$ and $R_b$ may together form a bond or a group $C_{1-6}$-alkylene;

$R_a$ and $R_c$ may together form a bond or a group $C_{1-6}$-alkylene;

$R_b$ and $R_c$ may together form a bond or a group $C_{1-6}$-alkylene;

$R_d$ represents a substituent chosen from a group $C_{1-6}$-alkyl, $C_{3-7}$-cycloalkyl, $C_{3-7}$-cycloalkyl-$C_{1-6}$-alkyl, hydroxy-$C_{1-6}$-alkyl, $C_{1-6}$-alkyloxy-$C_{1-6}$-alkyl, $C_{1-6}$-fluoroalkyl or benzyl;

$R_f$ represents a group $C_{1-6}$-alkyl, hydroxy-$C_{1-6}$-alkyl, $C_{1-6}$-alkyloxy-$C_{1-6}$-alkyl or $C_{1-6}$-fluoroalkyl;

$R_2$, $R_7$ and $R_8$ being as defined above.

Among the compounds of general formula (I) that are subjects of the invention, a sixth group of compounds is constituted by the compounds for which:

the cyclic amine formed by —N-A-L-B— represents a piperazinyl, octahydropyrrolopyrazinyl, diazabicycloheptyl or hexahydropyrrolopyrrolyl group, optionally substituted with one or more methyl, ethyl, propyl, isopropyl, cyclopropyl, methylpropyl, hydroxymethyl, hydroxyethyl, hydroxy(methyl)propyl, hydroxy(methyl)butyl, fluoromethyl, fluoroethyl or benzyl groups;

$R_2$, $R_7$ and $R_8$ being as defined above.

Among the compounds of general formula (I) that are subjects of the invention, a seventh group of compounds is constituted by the compounds for which:

the cyclic amine formed by —N-A-L-B— represents a piperazin-1-yl, 3-(R)-methylpiperazin-1-yl, 3,3-dimethylpiperazin-1-yl, cis-3,5-dimethylpiperazin-1-yl, 4-methylpiperazin-1-yl, 4-(2-hydroxyethyl)piperazin-1-yl, 4-(2-fluoroethyl)piperazin-1-yl, 4-isopropylpiperazin-1-yl, 4-cyclopropylpiperazin-1-yl, 4-benzylpiperazin-1-yl, 4-(2-hydroxy-2-methylpropyl)piperazin-1-yl, 4-(3-hydroxy-3-methylbutyl)piperazin-1-yl, (S)- octahydropyrrolo[1,2-a]pyrazin-2-yl, (1S,4S)-2,5- diazabicyclo[2.2.1]hept-2-yl, 5-(2-hydroxyethyl)-(1S,4S)-2,5-diazabicyclo[2.2.1]hept-2-yl, 5- isopropyl-(1S,4S)-2,5-diazabicyclo[2.2.1]hept-2-yl, hexahydropyrrolo[3,4-c]pyrrol-2-(1H)-yl, 5-methylhexahydropyrrolo[3,4-c]pyrrol-2-(1H)-yl, 5-(2-isopropyl)hexahydropyrrolo[3,4-c]pyrrol-2-(1H)-yl, 5-(2-hydroxyethyl)hexahydropyrrolo[3,4-c] pyrrol-2-(1H)-yl, 5-(benzyl)-hexahydropyrrolo[3,4-c] pyrrol-2-(1H)-yl, 3-(hydroxymethyl)piperazin-1-yl or 3-fluoromethylpiperazin-1-yl group;

$R_2$, $R_7$ and $R_8$ being as defined above.

Among the compounds of general formula (I) that are subjects of the invention, an eighth group of compounds is constituted by the compounds for which:

the cyclic amine formed by —N-A-L-B— represents a piperazinyl, octahydropyrrolopyrazinyl, diazabicycloheptyl or hexahydropyrrolopyrrolyl group, optionally substituted with one or more methyl, ethyl, propyl, isopropyl, cyclopropyl, methylpropyl, hydroxyethyl, hydroxy(methyl)propyl, hydroxy(methyl)butyl, fluoroethyl or benzyl groups;

$R_2$, $R_7$ and $R_8$ being as defined above.

Among the compounds of general formula (I) that are subjects of the invention, a ninth group of compounds is constituted by the compounds for which: the cyclic amine formed by —N-A-L-B— represents a piperazin-1-yl, 3-(R)-methylpiperazin-1-yl, 3,3-dimethylpiperazin-1-yl, cis-3,5-dimethylpiperazin-1-yl, 4-methylpiperazin-1-yl, 4-(2-hydroxyethyl)piperazin-1-yl, 4-(2-fluoroethyl)piperazin-1-yl, 4-isopropylpiperazin-1-yl, 4-cyclopropylpiperazin-1-yl, 4-benzylpiperazin-1-yl, 4-(2-hydroxy-2-methylpropyl)piperazin-1-yl, 4-(3-hydroxy-3-methylbutyl)piperazin-1-yl, (S)-octahydropyrrolo[1,2-a]pyrazin-2-yl, (1S,4S)-2,5-diazabicyclo[2.2.1]hept-2-yl, 5-(2-hydroxyethyl)-(1S,4S)-2,5-diazabicyclo[2.2.1]hept-2-yl, 5-isopropyl-(1S,4S)-2,5-diazabicyclo[2.2.1]hept-2-yl, hexahydropyrrolo[3,4-c]pyrrol-2-(1H)-yl, 5-methylhexahydropyrrolo[3,4-c]pyrrol-2-(1H)-yl, 5-(2-isopropyl)hexahydropyrrolo[3,4-c]pyrrol-2-(1H)-yl, 5-(2-hydroxyethyl)hexahydropyrrolo[3,4-c]pyrrol-2-(1H)-yl or 5-(benzyl)hexahydropyrrolo[3,4-c]pyrrol-2-(1H)-yl group;

$R_2$, $R_7$ and $R_8$ being as defined above.

Among the compounds of general formula (I) that are subjects of the invention, a tenth group of compounds is constituted by the compounds for which:

A represents a group $C_{1-7}$-alkylene;
B represents a group $C_{1-7}$-alkylene;
L represents a carbon atom substituted with two groups $R_{e2}$; the carbon atoms of A and of B being optionally substituted with one or more groups $R_f$, which may be identical to or different from each other;
$R_f$ represents a group $C_{1-6}$-alkyl;
Two groups $R_{e2}$ form, with the carbon atom which bears them, an azetidine, pyrrolidine, piperidine or morpholine group;

$R_2$, $R_7$ and $R_8$ being as defined above.

Among the compounds of general formula (I) that are subjects of the invention, an eleventh group of compounds is constituted by the compounds for which:

the cyclic amine formed by —N-A-L-B— represents a diazaspiroundecyl or oxadiazaspiroundecyl group;

$R_2$, $R_7$ and $R_8$ being as defined above.

Among the compounds of general formula (I) that are subjects of the invention, a twelfth group of compounds is constituted by the compounds for which:

the cyclic amine formed by —N-A-L-B— represents a 2,9-diazaspiro[5.5]undec-9-yl or 1-oxa-4,9-diazaspiro[5.5]undec-9-yl group;

$R_2$, $R_7$ and $R_8$ being as defined above.

Among the compounds of general formula (I) that are subjects of the invention, a thirteenth group of compounds is constituted by the compounds for which:

A represents a group $C_{1-7}$-alkylene;
B represents a group $C_{1-7}$-alkylene;
L represents a carbon atom substituted with a group $R_{e1}$ and a group $R_d$;
$R_d$ represents a hydrogen atom;
$R_{e1}$ represents a group —$NR_4R_5$ or a cyclic monoamine;
$R_4$ and $R_5$ represent, independently of each other, a hydrogen atom or a group $C_{1-6}$-alkyl, $C_{3-7}$-cycloalkyl or $C_{3-7}$-cycloalkyl-$C_{1-6}$-alkyl;

$R_2$, $R_7$ and $R_8$ being as defined above.

Among the compounds of general formula (I) that are subjects of the invention, a fourteenth group of compounds is constituted by the compounds for which:

the cyclic amine formed by —N-A-L-B— represents a pyrrolidine or piperidine group, substituted with a pyrrolidine group;

$R_2$, $R_7$ and $R_8$ being as defined above.

Among the compounds of general formula (I) that are subjects of the invention, a fifteenth group of compounds is constituted by the compound for which:

the cyclic amine formed by —N-A-L-B— represents a (R,S)-3-[pyrrolidin-1-yl]pyrrolidin-1-yl or 4-(pyrrolidin-1-yl)piperidin-1-yl group;

$R_2$, $R_7$ and $R_8$ being as defined above.

Among the compounds of general formula (I) that are subjects of the invention, a sixteenth group of compounds is constituted by the compounds for which:

$R_2$ represents a phenyl, 3-fluorophenyl, 4-fluorophenyl, 3,4-difluorophenyl, 3,5-difluorophenyl, 3,5-dichlorophenyl, 3,5-dimethylphenyl or 3,5-di(trifluoromethyl)phenyl group;
the cyclic amine formed by —N-A-L-B— represents a piperazin-1-yl, 3-(R)-methylpiperazin-1-yl, 3,3-dimethylpiperazin-1-yl, cis-3,5-dimethylpiperazin-1-yl, 4-methylpiperazin-1-yl, 4-(2-hydroxyethyl)piperazin-1-yl, 4-(2-fluoroethyl)piperazin-1-yl, 4-isopropylpiperazin-1-yl, 4-cyclopropylpiperazin-1-yl, 4-benzylpiperazin-1-yl, 4-(2-hydroxy-2-methylpropyl)piperazin-1-yl, 4-(3-hydroxy-3-methylbutyl)piperazin-1-yl, (S)-octahydropyrrolo[1,2-a]pyrazin-2-yl, (1S,4S)-2,5-diazabicyclo[2.2.1]hept-2-yl, 5-(2-hydroxyethyl)-(1S,4S)-2,5-diazabicyclo[2.2.1]hept-2-yl, 5-isopropyl-(1S,4S)-2,5-diazabicyclo[2.2.1]hept-2-yl, hexahydropyrrolo[3,4-c]pyrrol-2-(1H)-yl, 5-methyl-hexahydropyrrolo[3,4-c]pyrrol-2-(1H)-yl, 5-(2-isopropyl)hexahydropyrrolo[3,4-c]pyrrol-2-(1H)-yl, 5-(2-hydroxyethyl)hexahydropyrrolo[3,4-c]pyrrol-2-(1H)-yl, 5-(benzyl)hexahydro-pyrrolo[3,4-c]pyrrol-2-(1H)-yl, 3-(hydroxymethyl)piperazin-1-yl or 3-fluoromethylpiperazin-1-yl group;
$R_7$ and $R_8$ represent, independently of each other, a hydrogen atom or a methyl group.

Among the compounds of general formula (I) that are subjects of the invention, a seventeenth group of compounds is constituted by the compounds for which:

$R_2$ represents a phenyl, 3-fluorophenyl, 4-fluorophenyl, 3,4-difluorophenyl, 3,5-difluorophenyl, 3,5-dichlorophenyl, 3,5-dimethylphenyl or 3,5-di(trifluoromethyl)phenyl group;
the cyclic amine formed by —N-A-L-B— represents a piperazin-1-yl, 3-(R)-methylpiperazin-1-yl, 3,3-dimethylpiperazin-1-yl, cis-3,5-dimethylpiperazin-1-yl, 4-methylpiperazin-1-yl, 4-(2-hydroxyethyl)piperazin-1-yl, 4-(2-fluoroethyl)piperazin-1-yl, 4-isopropylpiperazin-1-yl, 4-cyclopropylpiperazin-1-yl, 4-benzylpiperazin-1-yl, 4-(2-hydroxy-2-methylpropyl)piperazin-1-yl, 4-(3-hydroxy-3-methylbutyl)piperazin-1-yl, (S)-octahydropyrrolo[1,2-a]pyrazin-2-yl, (1S,4S)-2,5-diazabicyclo[2.2.1]hept-2-yl, 5-(2-hydroxyethyl)-(1S,4S)-2,5-diazabicyclo[2.2.1]hept-2-yl, 5-isopropyl-(1S,4S)-2,5-diazabicyclo[2.2.1]hept-2-yl, hexahydropyrrolo[3,4-c]pyrrol-2-(1H)-yl, 5-methyl-hexahydropyrrolo[3,4-c]pyrrol-2-(1H)-yl, 5-(2-isopropyl)hexahydropyrrolo[3,4-c]pyrrol-2-(1H)-yl, 5-(2-hydroxyethyl)hexahydropyrrolo[3,4-c]pyrrol-2-(1H)-yl or 5-(benzyl)hexahydropyrrolo[3,4-c]pyrrol-2-(1H)-yl group;
$R_7$ and $R_8$ represent, independently of each other, a hydrogen atom or a methyl group.

Among the compounds of general formula (I) that are subjects of the invention, an eighteenth group of compounds is constituted by the compounds for which:

$R_2$ represents a 4-fluorophenyl group;
the cyclic amine formed by —N-A-L-B— represents a 2,9-diazaspiro[5.5]undec-3-yl or 1-oxa-4,9-diazaspiro[5.5]undec-9-yl group;
$R_7$ and $R_8$ represent a hydrogen atom.

Among the compounds of general formula (I) that are subjects of the invention, a nineteenth group of compounds is constituted by the compounds for which:

$R_2$ represents a 4-fluorophenyl, 3,5-difluorophenyl, 3,5-dichlorophenyl, 3,5-dimethylphenyl or 3,5-di(trifluoromethyl)phenyl group;
the cyclic amine formed by —N-A-L-B— represents a (R,S)-3-[pyrrolidin-1-yl]pyrrolidin-1-yl or 4-(pyrrolidin-1-yl)piperidin-1-yl group;
$R_7$ and $R_8$ represent a hydrogen atom.

Among the compounds of general formula (I) that are subjects of the invention, mention may in particular be made of the following compounds:

2-(4-fluorophenyl)-6-piperazin-1-yl-3-pyridazin-4-yl-imidazo[1,2-b]pyridazine;
2-(4-fluorophenyl)-6-((R)-3-methylpiperazin-1-yl)-3-pyridazin-4-yl-imidazo[1,2-b]pyridazine;
6-(3,3-dimethylpiperazin-1-yl)-2-(4-fluorophenyl)-3-pyridazin-4-yl-imidazo[1,2-b]pyridazine;
6-(cis-3,5-dimethylpiperazin-1-yl)-2-(4-fluorophenyl)-3-pyridazin-4-yl-imidazo[1,2-b]pyridazine;
2-(4-fluorophenyl)-6-(4-methylpiperazin-1-yl)-3-pyridazin-4-yl-imidazo[1,2-b]pyridazine
2-{4-[2-(4-fluorophenyl)-3-pyridazin-4-yl-imidazo[1,2-b]pyridazin-6-yl]piperazin-1-yl}-ethanol;
6-[4-(2-fluoroethyl)piperazin-1-yl]-2-phenyl-3-pyridazin-4-yl-imidazo[1,2-b]pyridazine;
6-[4-(2-fluoroethyl)piperazin-1-yl]-2-(4-fluorophenyl)-3-pyridazin-4-yl-imidazo[1,2-b]pyridazine;
6-(4-isopropylpiperazin-1-yl)-2-phenyl-3-pyridazin-4-yl-imidazo[1,2-b]pyridazine;
2-(3-fluorophenyl)-6-(4-isopropylpiperazin-1-yl)-3-pyridazin-4-yl-imidazo[1,2-b]pyridazine;
2-(4-fluorophenyl)-6-(4-isopropylpiperazin-1-yl)-3-pyridazin-4-yl-imidazo[1,2-b]pyridazine;
2-(4-fluorophenyl)-6-(4-isopropylpiperazin-1-yl)-7,8-dimethyl-3-pyridazin-4-yl-imidazo[1,2-b]pyridazine;
2-(3,5-dimethylphenyl)-6-(4-isopropylpiperazin-1-yl)-3-pyridazin-4-yl-imidazo[1,2-b]pyridazine;
2-(3,4-difluorophenyl)-6-(4-isopropylpiperazin-1-yl)-3-pyridazin-4-yl-imidazo[1,2-b]pyridazine;
2-(3,5-difluorophenyl)-6-(4-isopropylpiperazin-1-yl)-3-pyridazin-4-yl-imidazo[1,2-b]pyridazine;
2-(3,5-dichlorophenyl)-6-(4-isopropylpiperazin-1-yl)-3-pyridazin-4-yl-imidazo[1,2-b]pyridazine;
2-(3,5-di(trifluoromethyl)phenyl)-6-(4-isopropylpiperazin-1-yl)-3-pyridazin-4-yl-imidazo[1,2-b]pyridazine;
6-(4-cyclopropylpiperazin-1-yl)-2-(4-fluorophenyl)-3-pyridazin-4-yl-imidazo[1,2-b]pyridazine;
6-(4-benzylpiperazin-1-yl)-2-(4-fluorophenyl)-3-pyridazin-4-yl-imidazo[1,2-b]pyridazine;
1-{4-[2-(4-fluorophenyl)-3-pyridazin-4-yl-imidazo[1,2-b]pyridazin-6-yl]piperazin-1-yl}-2-methylpropan-2-ol;
4-{4-[2-(4-fluorophenyl)-3-pyridazin-4-yl-imidazo[1,2-b]pyridazin-6-yl]piperazin-1-yl}-2-methylbutan-2-ol;
2-(4-fluorophenyl)-6-(S)-hexahydropyrrolo[1,2-a]pyrazin-2-yl-3-pyridazin-4-yl-imidazo[1,2-b]pyridazine;
6-((1S,4S)-2,5-diazabicyclo[2.2.1]hept-2-yl)-2-(4-fluorophenyl)-3-pyridazin-4-yl-imidazo[1,2-b]pyridazine;
2-{5-[2-(4-fluorophenyl)-3-pyridazin-4-yl-imidazo[1,2-b]pyridazin-6-yl]-(1S,4S)-2,5-diazabicyclo[2.2.1]hept-2-yl}-ethanol;
2-(4-fluorophenyl)-6-(5-isopropyl-(1S,4S)-2,5-diazabicyclo[2.2.1]hept-2-yl)-3-pyridazin-4-yl-imidazo[1,2-b]pyridazine;
2-(4-fluorophenyl)-6-hexahydropyrrolo[3,4-c]pyrrol-2-(1H)-yl-3-pyridazin-4-yl-imidazo[1,2-b]pyridazine;
2-(4-fluorophenyl)-6-(5-methylhexahydropyrrolo[3,4-c]pyrrol-2-(1H)-yl)-3-pyridazin-4-yl-imidazo[1,2-b]pyridazine;
2-(4-fluorophenyl)-6-(5-isopropylhexahydropyrrolo[3,4-c]pyrrol-2-(1H)-yl)-3-pyridazin-4-yl-imidazo[1,2-b]pyridazine;
2-{(5-[2-(4-fluorophenyl)-3-pyridazin-4-yl-imidazo[1,2-b]pyridazin-6-yl]-hexahydro-pyrrolo[3,4-c]pyrrol-2-(1H)-yl}-ethanol;
2-(4-fluorophenyl)-6-(5-benzylhexahydropyrrolo[3,4-c]pyrrol-2-(1H)-yl)-3-pyridazin-4-yl-imidazo[1,2-b]pyridazine;
9-[2-(4-fluorophenyl)-3-pyridazin-4-yl-imidazo[1,2-b]pyridazin-6-yl]-2,9-diaza-spiro[5.5]undecane;
9-[2-(4-fluorophenyl)-3-pyridazin-4-yl-imidazo[1,2-b]pyridazin-6-yl]-1-oxa-4,9-diaza-spiro[5.5]undecane;
6-[1,3]bipyrrolidinyl-1'-yl-2-(4-fluorophenyl)-3-pyridazin-4-yl-imidazo[1,2-b]pyridazine;
2-(4-fluorophenyl)-3-pyridazin-4-yl-6-(4-pyrrolidin-1-yl-piperidin-1-yl)-imidazo[1,2-b]pyridazine;
2-(3,5-dimethylphenyl)-3-pyridazin-4-yl-6-(4-pyrrolidin-1-yl-piperidin-1-yl)-imidazo[1,2-b]pyridazine;
2-(3,5-difluorophenyl)-3-pyridazin-4-yl-6-(4-pyrrolidin-1-yl-piperidin-1-yl)-imidazo[1,2-b]pyridazine;
2-(3,5-dichlorophenyl)-3-pyridazin-4-yl-6-(4-pyrrolidin-1-yl-piperidin-1-yl)-imidazo[1,2-b]pyridazine;
2-(3,5-di(trifluoromethyl)phenyl)-3-pyridazin-4-yl-6-(4-pyrrolidin-1-yl-piperidin-1-yl)-imidazo[1,2-b]pyridazine;
(+/−)-{4-[2-(4-fluorophenyl)-3-pyridazin-4-ylimidazo[1,2-b]pyridazin-6-yl]piperazin-2-yl}methanol;
(+/−)-6-(3-fluoromethylpiperazin-1-yl)-2-(4-fluorophenyl)-3-pyridazin-4-ylimidazo[1,2-b]pyridazine;
6-(5-methylhexahydropyrrolo[3,4-c]pyrrol-2(1H)-yl)-2-phenyl-3-pyridazin-4-ylimidazo[1,2-b]pyridazine;
2-(3-fluorophenyl)-6-(5-methylhexahydropyrrolo[3,4-c]pyrrol-2(1H)-yl)-3-pyridazin-4-ylimidazo[1,2-b]pyridazine;
2-(4-fluorophenyl)-7-methyl-6-(5-methylhexahydropyrrolo[3,4-c]pyrrol-2-(1H)-yl)-3-pyridazin-4-ylimidazo[1,2-b]pyridazine;
2-(4-fluorophenyl)-8-methyl-6-(5-methylhexahydropyrrolo[3,4-c]pyrrol-2-(1H)-yl)-3-pyridazin-4-ylimidazo[1,2-b]pyridazine;
2-(3,4-difluorophenyl)-6-(5-methylhexahydropyrrolo[3,4-c]pyrrol-2(1H)-yl)-3-pyridazin-4-ylimidazo[1,2-b]pyridazine.

A subject of the invention is also a process for preparing the compounds of the invention of formula (I).

In accordance with the invention, the compounds of general formula (I) may be prepared according to the general process described in Scheme 1 below.

In general, as illustrated in Scheme 1, the 6-amino-3-(pyridazin-4-yl)imidazo[1,2-b]pyridazine derivatives of general formula (I) in which $R_2$, A, L, B, $R_7$ and $R_8$ are as defined above may be prepared from a (pyridazin-4-yl)imidazo[1,2-b]pyridazine derivative of general formula (IIa), in which $R_2$, $R_7$ and $R_8$ are as defined above and $X_6$ represents a leaving group such as a halogen, by treatment with an amine of general formula (IIb) in which A, L and B are as defined above. This reaction may be performed by heating the reagents in a polar solvent such as pentanol or dimethyl sulfoxide.

The 6-amino-3-(pyridazin-4-yl)imidazo[1,2-b]pyridazine derivatives of general formula (I), in which $R_2$, A, L, B, $R_7$ and $R_8$ are as defined above, may also be prepared by condensation between a pyridazin-3-ylamine derivative of general formula (IIIa) in which A, L, B, $R_7$ and $R_8$ are as defined above and a 2-bromo-2-(pyridazin-4-yl)ethan-1-one derivative of general formula (IIIb) in which $R_2$ is as defined above. This reaction may be performed by heating the reagents in a polar solvent such as aliphatic alcohols, for example ethanol or butanol.

SCHEME 1
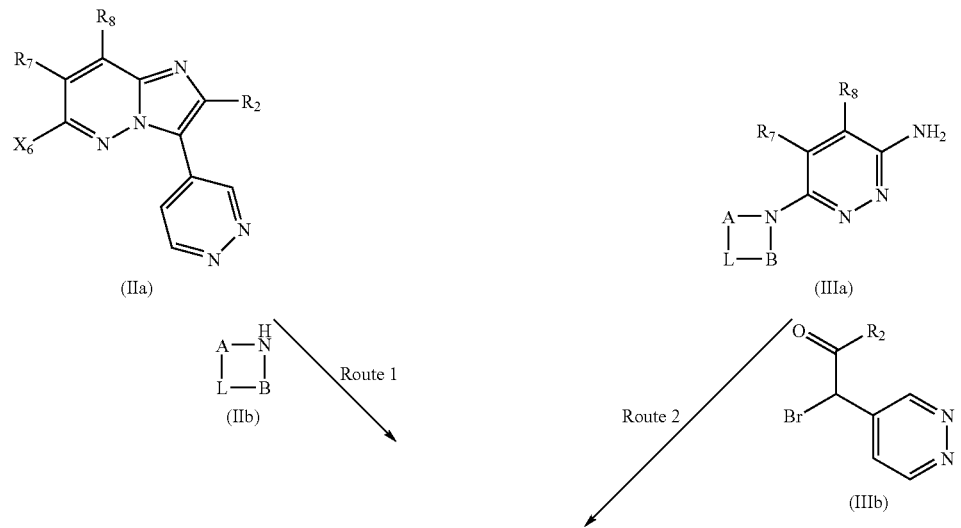
(IIa)    (IIIa)
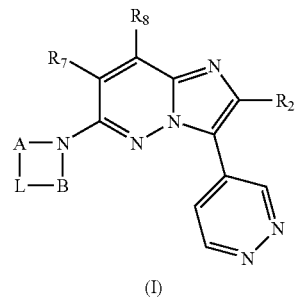
(IIb)    (IIIb)
Route 1    Route 2
(I)
M—R$_2$
(IVb)    Route 3
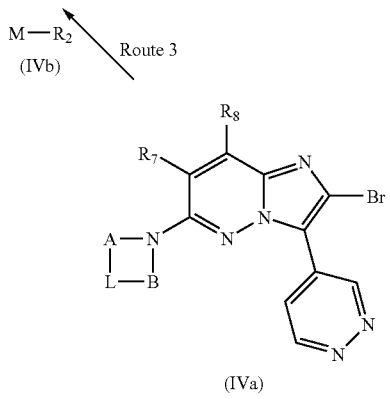
(IVa)

The 6-amino-3-(pyridazin-4-yl)imidazo[1,2-b]pyridazine derivatives of general formula (I), in which $R_2$, A, L, B, $R_7$ and $R_8$ are as defined above, may alternatively be prepared by metal-catalyzed coupling between a 2-bromo-3-(pyridazin-4-yl)imidazo[1,2-b]pyridazine derivative of general formula (IVa), in which A, L, B, $R_7$ and $R_8$ are as defined above, and an aryl derivative of general formula (IVb) in which $R_2$ is as defined above and M represents a trialkylstannyl group, most commonly a tributylstannyl group, or a dihydroxyboryl or dialkyloxyboryl group, most commonly a 4,4,5,5-tetramethyl-1,3,3,2-dioxaborolan-2-yl group, according to Stille or Suzuki conditions.

The couplings according to the Stille method are, for example, performed by heating in the presence of a catalyst such as tetrakis(triphenylphosphine)palladium and copper iodide, in a solvent such as N,N-dimethylacetamide.

The couplings according to the Suzuki method are, for example, performed by heating in the presence of a catalyst such as [1,1′-bis(diphenyl-phosphino)ferrocene]dichloropalladium, and of a mineral base such as cesium carbonate, in a solvent mixture such as dioxane and water.

Finally, the 6-amino-3-(pyridazin-4-yl)imidazo[1,2-b]pyridazine derivatives of general formula (I) may be prepared in two steps from a 6-aminoimidazo[1,2-b]pyridazine derivative of general formula (V) in which $R_2$, A, L, B, $R_7$ and $R_8$ are as defined above.

Thus, the reaction of a 6-aminoimidazo[1,2-b]pyridazine derivative of general formula (V) with pyridazine and an alkyl chloroformate derivative, for example ethyl chloroformate, leads to the derivative of general formula (VI) in which $R_2$, A, L, B, $R_7$ and $R_8$ are as defined above. The derivative of general formula (VI) is then oxidized using ortho-chloranil in a solvent such as toluene to give the 6-amino(pyridazin-4-yl)imidazo[1,2-b]pyridazine derivatives of general formula (I). In certain cases, the 6-amino-3-(pyridazin-4-yl)imidazo[1,2-b]pyridazine derivatives of general formula (I) for which the amine formed by N, L, A and B comprises a second secondary or tertiary amine may be prepared respectively from the corresponding primary or secondary amine by alkylation or reductive amination according to methods customary for those skilled in the art.

Synthesis of the Precursors

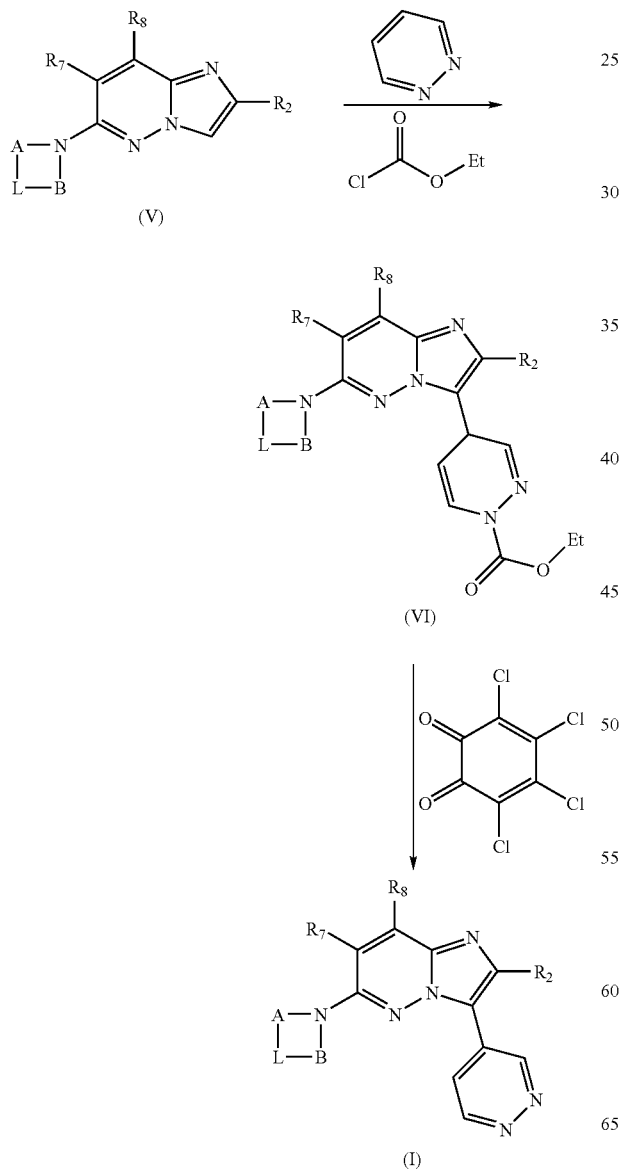

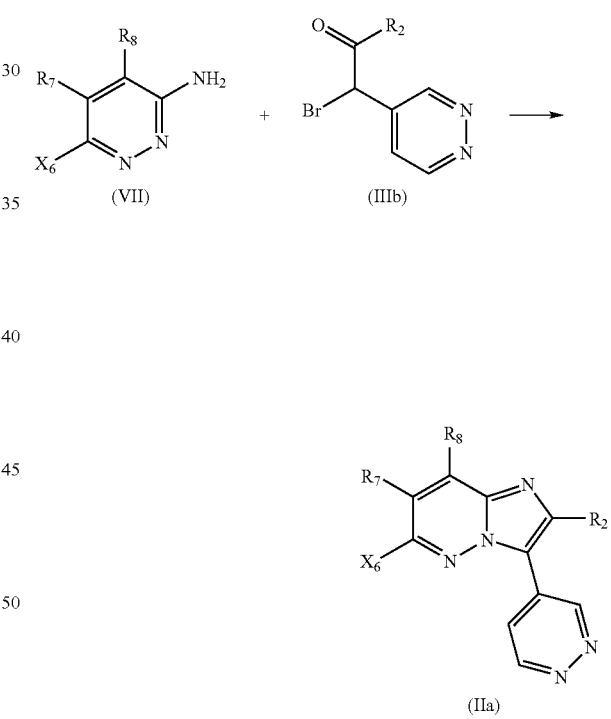

The 3-(pyridazin-4-yl)imidazo[1,2-b]pyridazine derivatives of general formula (IIa), in which $R_2$, $R_7$, $R_8$ and $X_6$ are as defined above, may be prepared by condensation between a pyridazin-3-ylamine derivative of general formula (VII), in which $R_7$ and $R_8$ are as defined above and $X_6$ represents a leaving group, and a 2-bromo-2-(pyridazin-4-yl)ethan-1-one derivative of general formula (IIIb) in which $R_2$ is as defined above.

The reaction may be performed by heating the reagents in a polar solvent such as aliphatic alcohols, for example ethanol or butanol.

SCHEME 4

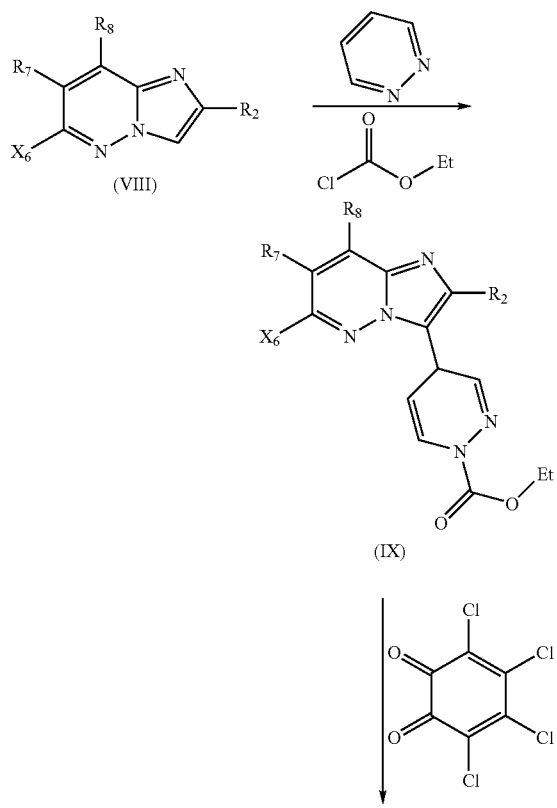
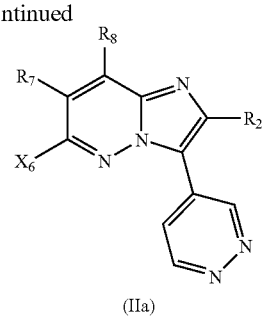

The 3-(pyridazin-4-yl)imidazo[1,2-b]pyridazine derivatives of general formula (IIa), in which $R_2$, $R_7$, $R_8$ and $X_6$ are as defined above, may also be prepared in two steps from an imidazo[1,2-b]pyridazine derivative of general formula (VIII) in which $X_6$, $R_2$, $R_7$ and $R_8$ are as defined above.

Thus, the reaction of an imidazo[1,2-b]pyridazine derivative of general formula (VIII) with pyridazine and an alkyl chloroformate, for example ethyl chloroformate, results in the derivative of general formula (IX) in which $X_6$, $R_2$, $R_7$ and $R_8$ are as defined above. The derivative of general formula (IX) is then oxidized using ortho-chloranil (in a solvent such as toluene to give the 3-(pyridazin-4-yl)imidazo[1,2-b]pyridazine derivatives of general formula (IIa).

The preparations of pyridazine derivatives of general formula (IIIa) in which A, L, B, $R_7$ and $R_8$ are as defined above or of 6-amino-imidazo[1,2-b]pyridazine derivatives of general formula (V) may be carried out according to the methods described in documents DE-2737542 and DE-3542661 or else according to similar methods well known to those skilled in the art.

SCHEME 5

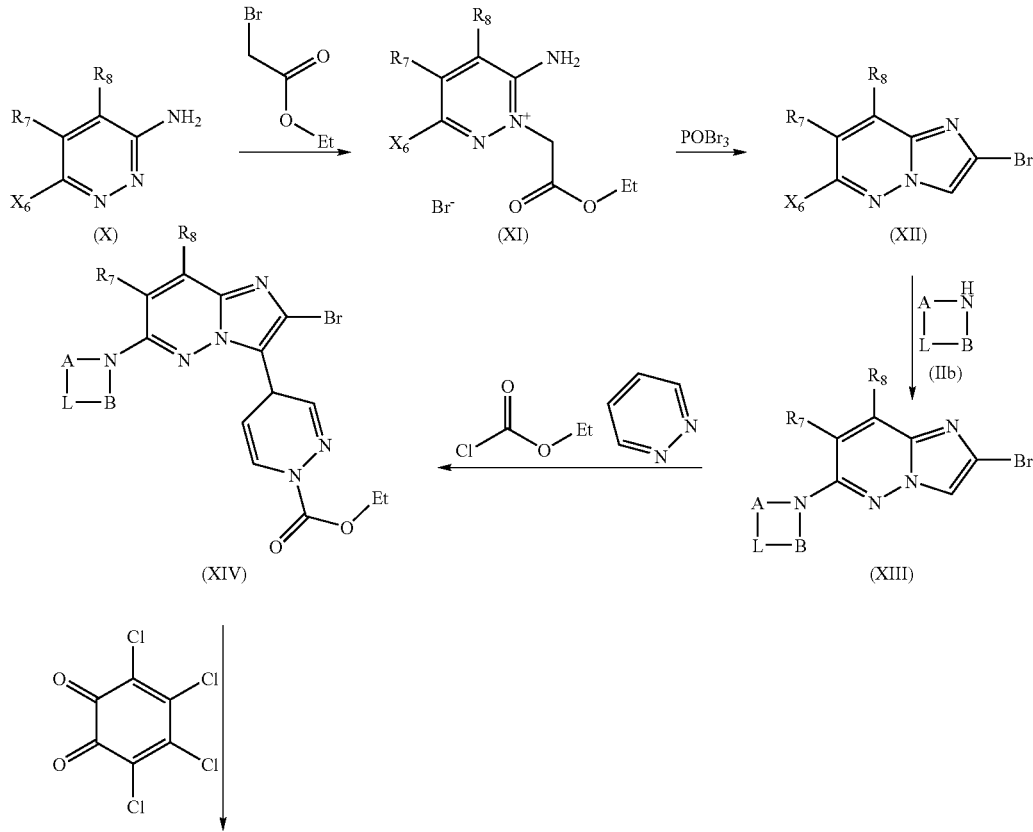

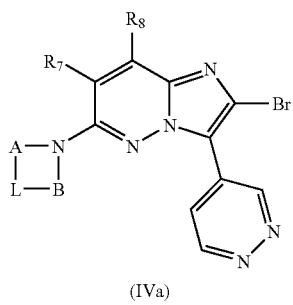

(IVa)

The 2-bromo-3-(pyridazin-4-yl)imidazo[1,2-b]pyridazine derivatives of general formula (IVa) in which $R_7$, $R_8$, A, L and B are as defined above may be prepared in five steps from a 3-amino-6-halopyridazine derivative of general formula (X) in which $X_6$, $R_7$ and $R_8$ are as defined above.

Thus, the alkylation of a 3-amino-6-halopyridazine derivative of general formula (X) using an alkyl 2-bromoacetate such as ethyl 2-bromoacetate, by heating in a polar solvent such as ethanol, results in the hydrobromide of formula (XI) in which $X_6$, $R_7$ and $R_8$ are as defined above. The latter is cyclized by heating in the presence of phosphorus oxybromide in an aprotic solvent such as toluene, so as to give a 6-halo-2-bromoimidazo[1,2-b]pyridazine derivative of general formula (XII) in which $X_6$, $R_7$ and $R_8$ are as defined above.

Said derivative is then treated by heating with an amine of general formula (IIb) in which A, L and B are as defined above, to give a 6-amino-2-bromoimidazo[1,2-b]pyridazine of general structure (XIII) in which A, L, B, $R_7$ and $R_8$ are as defined above.

This derivative is treated with pyridazine and an alkyl chloroformate, for example ethyl chloroformate, to give the derivative of general formula (XIV) in which A, L, B, $R_7$ and $R_8$ are as defined above. Finally, the derivative of general formula (XIV) is oxidized with ortho-chloranil in a solvent such as toluene to give the 6-amino(pyridazin-4-yl)imidazo[1,2-b]pyridazine derivatives of general formula (IVa).

In the preceding text, the term "leaving group" is intended to mean a group that can be readily cleaved from a molecule by heterolytic bond breaking, with the departure of a pair of electrons. This group can, for example, thus be readily replaced with another group in a substitution reaction. Such leaving groups are, for example, halogens or an activated hydroxy group such as a methyl, tosyl, triflate, acetyl, etc. Examples of leaving groups and also references for the preparation thereof are given in "Advances in Organic Chemistry", J. March, 3$^{rd}$ Edition, Wiley Interscience, p. 310-316.

Protecting Groups

For the compounds of general formula (I) or (IIIa) as defined above and when the group N-A-L-B comprises a primary or secondary amine function, this function may optionally be protected, during the synthesis, with a protecting group, for example a benzyl or a t-butyoxycarbonyl.

The products of general structure (I) as defined above are obtained according to the processes described, after a final additional step of deprotection of the protecting group according to the usual conditions known to those skilled in the art.

The following examples describe the preparation of certain compounds in accordance with the invention. These examples are not limiting and serve merely to illustrate the invention. The numbers of the compounds exemplified refer to those given in Table 1 hereinafter, which illustrate the chemical structures and the physical properties, respectively, of a number of compounds according to the invention.

EXAMPLE 1

Compound No. 30: 6-(5-benzylhexahydropyrrolo[3,4-c]pyrrol-2-(1H)-yl)-2-(4-fluorophenyl)-3-pyridazin-4-ylimidazo[1,2-b]pyridazine

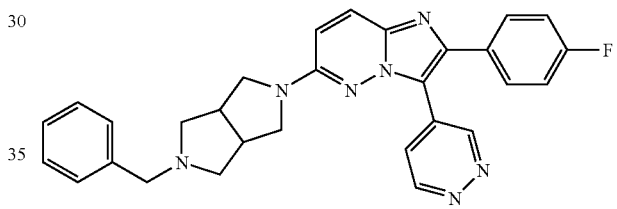

Step 1.1. Ethyl 4-[6-chloro-2-(4-fluorophenyl)-imidazo[1,2-b]pyridazin-3-yl]-4H-pyridazine-1-carboxylate

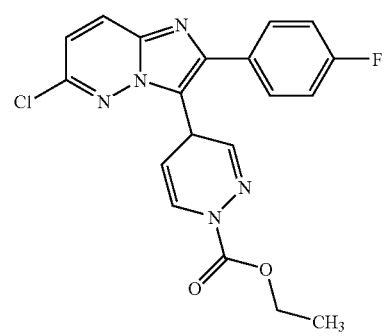 [SMILES: CCOC(=O)N1C=CC(c2c(-c3ccc(F)cc3)nc3ccc(Cl)nn23)C=N1]

2.90 ml (30.3 mmol) of ethyl chloroformate are added, dropwise in 30 minutes, to a solution of 3.00 g (12.1 mmol) of 6-chloro-2-(4-fluorophenyl)imidazo[1,2-b]pyridazine (CAS: 244081-70-7) and 4.40 ml (60.6 mmol) of pyridazine in 40 ml of dichloromethane at 10° C. The medium is stirred at 10° C. for a further hour and then left to stir for 3 hours. It is then poured into ice-cold water and the product is extracted with ethyl acetate.

The organic phase is dried over sodium sulfate and the solvent is concentrated under reduced pressure. The product is chromatographed on a silica gel column, elution being carried out with a mixture of aqueous ammonia, methanol and dichloromethane (0.2/2/98), to give 2.3 g of orangey foam containing the product with sufficient purity to be used in the following step.

$^1$H NMR (CDCl$_3$) δ: 7.9 (m, 1H); 7.5-7.6 (m, 2H); 7.0-7.2 (m, 5H); 6.75 (m, 1H); 5.9 (2m, 1H); 5.0-4.8 (2m, approximately 2H); 4.35 (m, >2H); 1.35 (m, >3H) ppm.

Step 1.2. 6-chloro-2-(4-fluorophenyl)-3-(pyridazin-4-yl)-imidazo[1,2-b]pyridazine

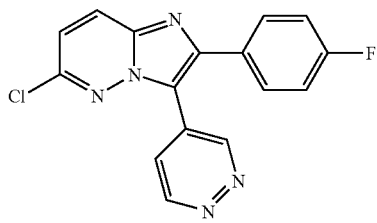 [SMILES: Fc1ccc(-c2nc3ccc(Cl)nn3c2-c2ccnnc2)cc1]

2.30 g (5.75 mmol) of the product obtained in the preceding step are dissolved in 30 ml of toluene and 1.66 g (6.33 mmol) of ortho-chloranil in solution in toluene are added.

The reaction medium is stirred for 30 minutes at ambient temperature and then poured into a 2N aqueous solution of sodium hydroxide. The product is extracted with ethyl acetate.

The organic phase is dried over sodium sulfate and then concentrated under reduced pressure. The product is chromatographed on a silica gel column, elution being carried out with a mixture of aqueous ammonia, methanol and dichloromethane (0.2/2/98), to give 1.0 g of white solid.

$^1$H NMR (CDCl$_3$) δ: 9.35 (d, 1H); 9.25 (d, 1H); 7.95 (d, 1H); 7.85 (d, 1H); 7.55 (m, 2H); 7.0-7.2 (m, 3H) ppm.

Step 1.3. 6-(5-benzylhexahydropyrrolo[3,4-c]pyrrol-2-(1H)-yl)-2-(4-fluorophenyl)-3-pyridazin-4-ylimidazo[1,2-b]pyridazine

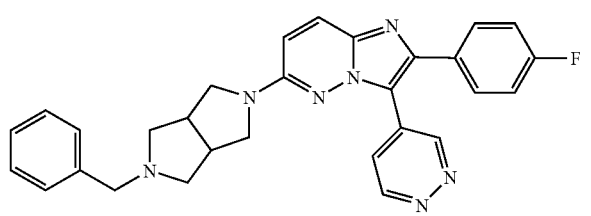 [SMILES: Fc1ccc(-c2nc3ccc(N4CC5CN(Cc6ccccc6)CC5C4)nn3c2-c2ccnnc2)cc1]

The mixture of 0.90 g (2.8 mmol) of 6-chloro-2-(4-fluorophenyl)-3-(pyridazin-4-yl)-imidazo[1,2-b]pyridazine and 1.7 g (8.3 mmol) of 5-benzyloctahydropyrrolo[3,4-c]pyrrole in 15 ml of pentanol is heated in a sealed tube at 150° C. for 18 hours. The reaction medium is poured into a 1N aqueous solution of hydrochloric acid and the aqueous phase is washed with ethyl acetate. The aqueous phase is then basified using aqueous sodium hydroxide and the product is extracted with dichloromethane. The organic phase is dried over sodium sulfate and then concentrated under reduced pressure.

The product is chromatographed on a silica gel column, elution being carried out with a mixture of aqueous ammonia, methanol and dichloromethane (0.2/2/98), to give 1.2 g of solid in the form of an amorphous white foam.

$^1$H NMR (CDCl$_3$) δ: 9.60 (d, 1H); 9.10 (d, 1H); 7.75 (m, 1H); 7.70 (d, 1H); 7.5 (m, 2H); 7.2 (m, 5H); 6.80 (d, 1H); 3.6-3.7 (m, 2H); 3.50 (s, 2H); 3.3 (m, 2H); 2.9 (m, 2H); 2.4-2.7 (d, 1H) ppm.

EXAMPLE 2

Compound No. 26: 2-(4-fluorophenyl)-6-(hexahydropyrrolo[3,4-c]pyrrol-2-(1H)-yl)-3-(pyridazin-4-yl)-imidazo[1,2-b]pyridazine

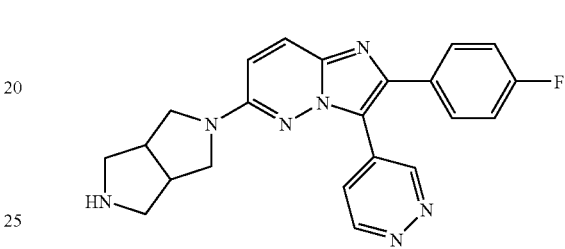

The mixture of 1.2 g (2.4 mmol) of 6-(5-benzylhexahydropyrrolo[3,4-c]pyrrol-2-(1H)-yl)-2-(4-fluorophenyl)-3-(pyridazin-4-yl)-imidazo[1,2-b]pyridazine and 2.3 g (36 mmol) of ammonium formate in 40 ml of methanol is refluxed for 2 hours in the presence of palladium-on-charcoal (10%) containing 50% moisture.

The reaction medium is concentrated under reduced pressure, and the residue is taken up with dichloromethane and washed with water. The organic phase is dried over sodium sulfate and then concentrated under reduced pressure. The product is chromatographed on a silica gel column, elution being carried out with a mixture of methanol and dichloromethane (10/90), to give 0.60 g of a white solid.

Mp: 130-135° C.

$^1$H NMR (CDCl$_3$) δ: 9.75 (d, 1H); 9.20 (d, 1H); 7.8 (m, 2H); 7.60 (m, 2H); 7.5 (m, 2H); 7.1 (m, 2H); 6.80 (d, 1H); 3.7 (m, 2H); 3.40 (dd, 2H); 3.2 (m, 2H); 2.8-3.1 (m, 4H); 2.7 (broad signal) ppm.

EXAMPLE 3

Compound No. 12: 2-(4-fluorophenyl)-6-(4-isopropylpiperazin-1-yl)-7,8-dimethyl-3-pyridazin-4-ylimidazo[1,2-b]pyridazine

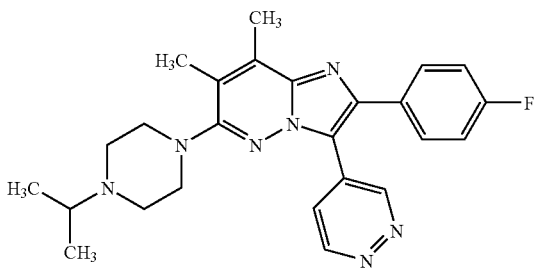 [SMILES: Cc1c(N2CCN(C(C)C)CC2)nn2c(-c3ccnnc3)c(-c3ccc(F)cc3)nc2c1C]

Step 3.1. 6-chloro-2-(4-fluorophenyl)-7,8-dimethylimidazo[1,2-b]pyridazine

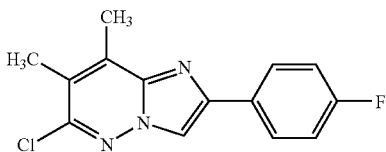 [SMILES: Cc1c(Cl)nn2cc(-c3ccc(F)cc3)nc2c1C]

The mixture of 13.0 g (82.5 mmol) of 6-chloro-4,5-dimethylpyridazin-3-ylamine and 23.2 g (107 mmol) of 2-bromo-1-(4-fluorophenyl)ethanone in 130 ml of ethanol is refluxed for 16 hours. The solvent is evaporated off under reduced pressure, and the residue is taken up with chloroform and washed with a dilute solution of aqueous ammonia. The organic phase is dried over sodium sulfate and then concentrated under reduced pressure. The brown solid obtained is triturated in acetone, to give 19.2 g of a beige powder after filtration and drying.

Mp: 172-174° C.

$^1$H NMR (CDCl$_3$) δ: 8.10 (s, 1H); 8.00 (pseudo dd, 1H); 7.15 (pseudo t, 1H); 2.70 (s, 3H); 2.4 (s, 3H) ppm

Step 3.2. Ethyl 4-[6-chloro-2-(4-fluorophenyl)-7,8-dimethylimidazo[1,2-b]pyridazin-3-yl]-4H-pyridazine-1-carboxylate

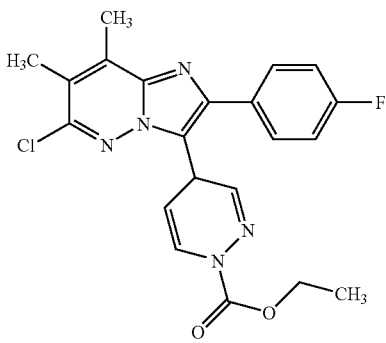 [SMILES: CCOC(=O)N1C=CC(c2c(-c3ccc(F)cc3)nc3c(C)c(C)c(Cl)nn23)C=N1]

7.8 ml (82 mmol) of ethyl chloroformate are added, dropwise, to a suspension of 9.00 g (32.6 mmol) of 6-chloro-2-(4-fluorophenyl)-7,8-dimethylimidazo[1,2-b]pyridazine and 11.9 ml (163 mmol) of pyridazine in 160 ml of dichloromethane at 10° C. The medium is stirred at 10° C. for a further hour and then left to stir for 3 hours. It is then poured into ice-cold water and the product is extracted with ethyl acetate. After several washes with water, the organic phase is dried over sodium sulfate and the solvent is concentrated under reduced pressure. The black residue is then solubilized in dichloromethane and stirred in the presence of animal charcoal, to give a dark-brown solid after filtration through a Büchner funnel and evaporation of the solvent under reduced pressure. The product is chromatographed on a neutral alumina column, elution being carried out with a mixture of dichloromethane and petroleum ether (80/20), to give 11.5 g of a beige powder after crystallization from diethyl ether and drying.

Mp: 159-161° C.

$^1$H NMR (CDCl$_3$) δ: 7.65 (m, 2H); 7.1-7.25 (m, 3H); 6.8 (m, 1H); 5.0 (m, 1H); 4.90 (m, 1H); 4.45 (q, 2H); 2.70 (s, 3H); 2.45 (s, 3H); 1.40 (m, 3H) ppm.

Step 3.3. 6-chloro-2-(4-fluorophenyl)-7,8-dimethyl-3-pyridazin-4-ylimidazo[1,2-b]pyridazine

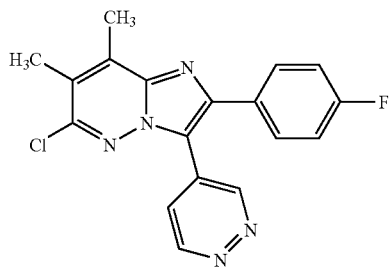 [SMILES: Cc1c(Cl)nn2c(-c3ccnnc3)c(-c3ccc(F)cc3)nc2c1C]

11.5 g (5.6 mmol) of ethyl 4-[6-chloro-2-(4-fluorophenyl)-7,8-dimethylimidazo[1,2-b]pyridazin-3-yl]-4H-pyridazine-1-carboxylate are dissolved in 300 ml of toluene and approximately 50 ml of chloroform. 7.3 g (30 mmol) of ortho-chloranil are then added portionwise with vigorous stirring.

The reaction medium is stirred for 1 hour at ambient temperature and then poured into a 2N aqueous solution of sodium hydroxide. The product is extracted with dichloromethane.

The organic phase is dried over sodium sulfate and then concentrated under reduced pressure. The black solid obtained is chromatographed on a silica gel column, elution being carried out with a mixture of aqueous ammonia, methanol and dichloromethane (0.2/2/98), to give 6.0 g of a beige powder.

Mp: 276-278° C.

$^1$H NMR (CDCl$_3$) δ: 9.40 (d, 1H); 9.30 (dd, 1H); 7.95 (dd, 1H); 7.65 (m, 2H); 7.15 (pt, 2H); 2.80 (s, 3H); 2.50 (s, 3H) ppm.

Step 3.4. 2-(4-fluorophenyl)-6-(4-isopropylpiperazin-1-yl)-7,8-dimethyl-3-pyridazin-4-ylimidazo[1,2-b]pyridazine

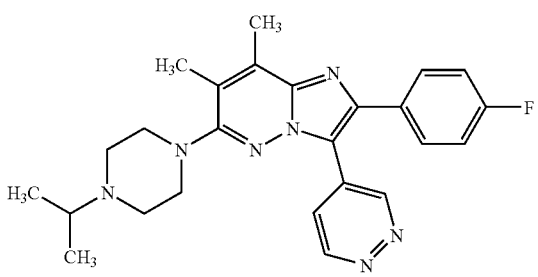 [SMILES: Cc1c(N2CCN(C(C)C)CC2)nn2c(-c3ccnnc3)c(-c3ccc(F)cc3)nc2c1C]

The mixture of 0.40 g (1.1 mmol) of 6-chloro-2-(4-fluorophenyl)-7,8-dimethyl-3-pyridazin-4-ylimidazo[1,2-b]pyridazine, 0.16 ml (1.1 mmol) of triethylamine and 0.29 g (2.3 mmol) of 1-isopropylpiperazine in 4 ml of pentanol is microwave-heated at 180° C. (300 W) for 6 hours.

The reaction medium is poured into a 1N aqueous solution of hydrochloric acid and the aqueous phase is washed with ethyl acetate. The aqueous phase is then basified using aqueous ammonia and the product is extracted with dichloromethane. The organic phase is dried over sodium sulfate and then concentrated under reduced pressure. The brown solid obtained is chromatographed on a silica gel column, elution being carried out with a mixture of aqueous ammonia, methanol and dichloromethane (0.3/3/97), to give 0.39 g of a white solid.

Mp: 222-224° C.

$^1$H NMR (CDCl$_3$) δ: 9.50 (d, 1H); 9.20 (d, 1H); 7.90 (dd, 1H); 7.75 (m, 1H); 7.5 (m, 2H); 7.15 (pt, 2H); 3.2 (m, 4H); 2.75 (m, 5H); 2.65 (s, 3H); 2.50 (s, 3H); 1.15 (d, 6H) ppm.

EXAMPLE 4

Compound No. 19: 2-(4-fluorophenyl)-6-(4-benzylpiperazin-1-yl)-3-(pyridazin-4-yl)-imidazo[1,2-b]pyridazine

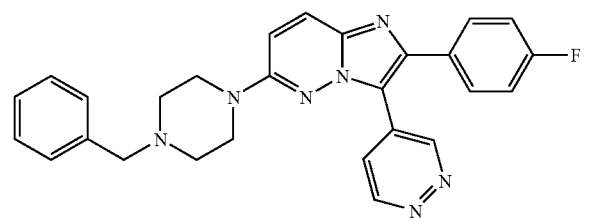 [SMILES: Fc1ccc(-c2nc3ccc(N4CCN(Cc5ccccc5)CC4)nn3c2-c2ccnnc2)cc1]

Step 4.1.
6-(4-benzylpiperazin-1-yl)pyridazin-3-ylamine

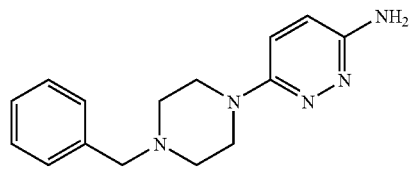 [SMILES: Nc1ccc(N2CCN(Cc3ccccc3)CC2)nn1]

48.9 g (278 mmol) of 1-benzylpiperazine and 12.0 g (92.6 mmol) of 3-amino-6-chloropyridazine are heated at 160° C. for 1 hour. The brown oil obtained is poured into 500 ml of an aqueous solution of sodium bicarbonate and the product is extracted with dichloromethane. The organic phase is dried and then concentrated under reduced pressure. The oil obtained is triturated in diethyl ether and 20.5 g of a solid are isolated after filtration and drying.

$^1$H NMR (CDCl$_3$) δ: 7.45-7.65 (m, 6H); 7.20 (s, 1H); 5.5 (broad unresolved peak, 2H); 3.80 (s, 2H); 3.60-3.75 (m, 4H); 2.80-2.85 (m, 4H) ppm.

Step 4.2.
1-(4-fluorophenyl)-2-pyridazin-4-ylethanone

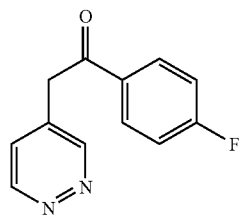 [SMILES: O=C(Cc1ccnnc1)c1ccc(F)cc1]

A solution under argon of 1.88 g (20.0 mmol) of 4-methylpyridazine and 3.36 g (20.0 mmol) of ethyl 4-fluorobenzoate in 50 ml of anhydrous tetrahydrofuran is cooled to 0° C. and then 20.0 ml (40.0 mmol) of a 2M solution of sodium hexamethyldisilazane in tetrahydrofuran (THF) are added dropwise. After the addition, the temperature is allowed to return to ambient temperature, while a gradual setting of the reaction medium is observed. After one hour, the mixture is poured into an aqueous solution of ammonium chloride and the product is extracted with ethyl acetate. The organic phase is dried over sodium sulfate, filtered and concentrated under reduced pressure to give an orangey-red solid. The latter is triturated at reflux in 80 ml of diisopropyl ether containing a few ml of isopropyl alcohol and the solid is then isolated by filtration after cooling to 0° C. 3.35 g of a pale yellow powder are thus isolated after drying.

$^1$H NMR (CDCl$_3$) δ: 9.20 (m, 2H); 8.10 (dd, 2H); 7.50 (dd, 2H); 7.2 (d, 2H); 4.35 (s, 2H) ppm.

Step 4.3. 2-bromo-1-(4-fluorophenyl)-2-pyridazin-4-ylethanone

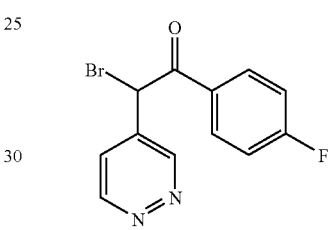

0.70 g (5.2 mmol) of sodium acetate is added to a solution of 1.02 g (4.70 mmol) of 1-(4-fluorophenyl)-2-pyridazin-4-ylethanone in 20 ml of acetic acid and then 0.26 ml (5.2 mmol) of bromine in solution in a few ml of acetic acid is added dropwise (slight exotherm). After 30 minutes at ambient temperature, the reaction medium is cooled and 60 ml of water are added. The product is extracted with diethyl ether. The cooled organic phase is washed with an aqueous solution of sodium hydrogen carbonate, dried over sodium sulfate and filtered. This solution (approximately 50 ml) is used rapidly, as it is, in the rest of the synthesis.

Step 4.4. 6-(4-benzylpiperazin-1-yl)-2-(4-fluorophenyl)-3-pyridazin-4-yl-imidazo[1,2-b]pyridazine

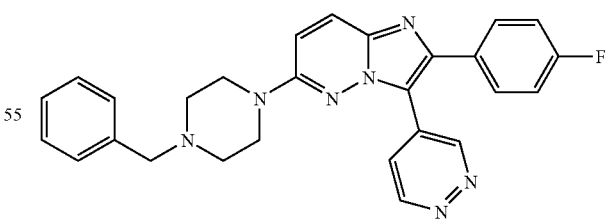

The ethereal solution of 2-bromo-1-(4-fluorophenyl)-2-pyridazin-4-ylethanone obtained previously (approximately 50 ml) is added, with precautions being taken, to a solution of 1.30 g (4.41 mmol) of 6-(4-benzylpiperazin-1-yl)pyridazin-3-ylamine in 50 ml of butanol. The diethyl ether is separated by distillation and the mixture is stirred at reflux for more than one hour. After cooling, the mixture is poured into a saturated solution of sodium bicarbonate, the product is extracted with ethyl acetate and the solution is concentrated under reduced pressure. The brown oil obtained is taken up with a 3N aqueous solution of hydrochloric acid and this solution is washed with diethyl ether and basified with aqueous ammonia. The product is finally extracted with chloroform, and the organic phase is dried over sodium sulfate, filtered and concentrated under reduced pressure. 1.6 g of a brown foam are obtained, which foam is chromatographed on silica gel, elution being carried out with a mixture of aqueous ammonia, methanol and dichloromethane (0.7/7/93), to give 0.6 g of a yellowish solid.

Mp: 198-201° C.

$^1$H NMR (CDCl$_3$) δ: 9.55 (d, 1H); 9.20 (d, 1H); 7.85 (d, 1H); 7.75 (m, 1H); 7.60 (m, 2H); 7.35 (m, 5H); 7.1 (m, 2H); 7.0 (m, 1H); 3.6 (m, 6H); 3.50 (s, 2H); 2.6 (m, 4H) ppm.

EXAMPLE 5

Compound No. 1: 2-(4-fluorophenyl)-6-(piperazin-1-yl)-3-(pyridazin-4-yl)imidazo[1,2-b]pyridazine

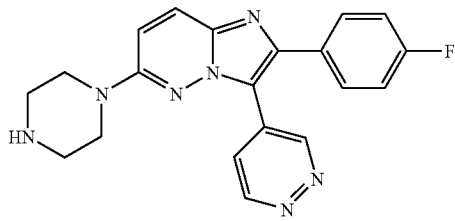 [SMILES: Fc1ccc(-c2nc3ccc(N4CCNCC4)nn3c2-c2ccnnc2)cc1]

The mixture of 0.40 g (0.86 mmol) of 6-(4-benzylpiperazin-1-yl)-2-(4-fluorophenyl)-3-(pyridazin-4-yl)imidazo[1,2-b]pyridazine, 0.81 g (13 mmol) of ammonium formate and 0.5 g of palladium-on-charcoal (10%) containing 50% moisture in 60 ml of methanol is stirred at reflux for 15 minutes.

The solvent is then eliminated by distillation under reduced pressure and the residue obtained is taken up with a 3N aqueous solution of hydrochloric acid and this solution is washed with diethyl ether and basified with aqueous ammonia. The product is finally extracted with dichloromethane, and the organic phase is dried over sodium sulfate, filtered and concentrated under reduced pressure. 0.27 g of a yellowish solid is obtained, which is chromatographed on silica gel, elution being carried out with a mixture of aqueous ammonia, methanol and dichloromethane (1/10/90), to give 0.15 g of a yellowish solid.

The latter is recrystallized from 25 ml of acetonitrile at reflux, and butanol is added thereto until solubilization is obtained. 0.11 g of a solid is finally isolated after filtration and drying.

Mp: 240-246° C.

$^1$H NMR (CDCl$_3$) δ: 9.60 (d, 1H); 9.20 (dd, 1H); 7.85 (d, 1H); 7.75 (m, 1H); 7.60 (m, 2H); 6.95-7.15 (m, 3H); 3.55 (m, 4H); 3.05 (m, 4H); 2.1 (sl, 1H) ppm.

EXAMPLE 6

Compound No. 11: 2-(4-fluorophenyl)-6-(4-isopropyl-piperazin-1-yl)-3-(pyridazin-4-yl)imidazo[1,2-b]pyridazine

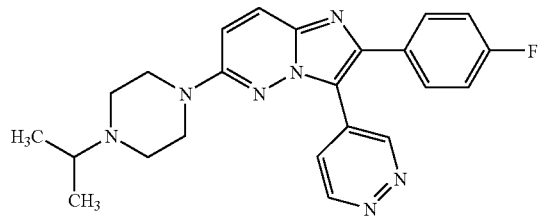 [SMILES: CC(C)N1CCN(c2ccc3nc(-c4ccc(F)cc4)c(-c4ccnnc4)n3n2)CC1]

The mixture of 0.26 g (0.8 mmol) of 6-chloro-2-(4-fluorophenyl)-3-(pyridazin-4-yl)imidazo[1,2-b]pyridazine and 0.66 g (3.2 mmol) of 1-isopropylpiperazine in 6 ml of pentanol is heated in a sealed tube at 130° C. for 10 hours.

The solvent is evaporated off under reduced pressure and the residue is taken up with dichloromethane and the organic phase is washed with an aqueous solution of sodium hydrogen carbonate. The organic phase is dried over sodium sulfate and then concentrated under reduced pressure. The product is chromatographed on a silica gel column, elution being carried out with a mixture of aqueous ammonia, methanol and dichloromethane (2/4/96), to give 0.25 g of a beige solid after crystallization from diisopropyl ether and drying.

Mp: 172-174° C.

$^1$H NMR (DMSO d6) δ: 9.30 (d, 1H); 9.25 (d, 1H); 8.00 (d, 1H); 7.90 (dd, 1H); 7.55 (m, 2H); 7.35 (d, 1H); 7.20 (pseudo t, 2H); 3.45 (m, 4H); 2.65 (m, 1H); 2.55 (m, 4H); 1.00 (d, 6H) ppm.

EXAMPLE 7

Compound No. 2: 2-(4-fluorophenyl)-6-((R)-3-methylpiperazin-1-yl)-3-(pyridazin-4-yl)imidazo[1,2-b]pyridazine

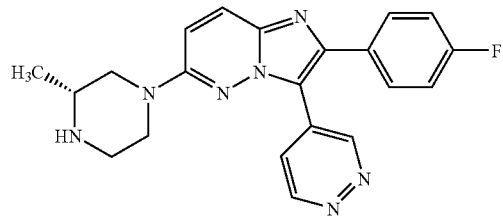 [SMILES: C[C@@H]1CN(c2ccc3nc(-c4ccc(F)cc4)c(-c4ccnnc4)n3n2)CCN1]

The mixture of 0.26 g (0.8 mmol) of 6-chloro-2-(4-fluorophenyl)-3-(pyridazin-4-yl)imidazo[1,2-b]pyridazine and 0.32 g (3.2 mmol) of (R)-3-methylpiperazine in 4 ml of pentanol is heated in a sealed tube at 130° C. for 32 hours.

The solvent is evaporated off under reduced pressure and the residue is taken up with dichloromethane and the organic phase is washed with an aqueous solution of sodium hydrogen carbonate. The organic phase is dried over sodium sulfate and then concentrated under reduced pressure. The product is chromatographed on a silica gel column, elution being carried out with a mixture of aqueous ammonia, methanol and dichloromethane (2/4/96), to give 0.24 g of a beige solid after crystallization from diisopropyl ether and drying.

Mp: 162-164° C.

[Alpha]$_D$=−7.9° (c=0.44, MeOH)

$^1$H NMR (DMSO d6) δ: 9.35 (d, 1H); 9.25 (d, 1H); 7.95 (d, 1H); 7.85 (dd, 1H); 7.55 (m, 2H); 7.35 (d, 1H); 7.25 (pseudo t, 2H); 3.95 (m, 2H); 2.65-3.05 (m, 5H); 1.00 (d, 3H) ppm.

EXAMPLE 8

Compound No. 6: 2-{4-[2-(4-fluorophenyl)-3-(pyridazin-4-yl)imidazo[1,2-b]pyridazin-6-yl]piperazin-1-yl}ethanol

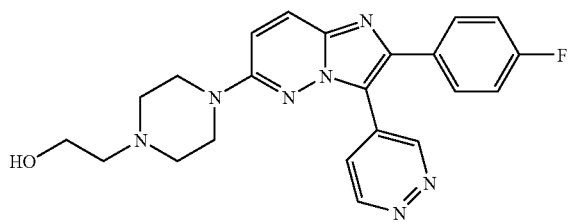 [SMILES: OCCN1CCN(c2ccc3nc(-c4ccc(F)cc4)c(-c4ccnnc4)n3n2)CC1]

The mixture of 0.26 g (0.8 mmol) of 6-chloro-2-(4-fluorophenyl)-3-(pyridazin-4-yl)imidazo[1,2-b]pyridazine and 0.425 g (3.2 mmol) of 2-hydroxyethylpiperazine in 4 ml of pentanol is heated in a sealed tube at 130° C. for 32 hours.

The solvent is evaporated off under reduced pressure and the residue is taken up with dichloromethane and the organic phase is washed with an aqueous solution of sodium hydrogen carbonate. The organic phase is dried over sodium sulfate and then concentrated under reduced pressure. The product is chromatographed on a silica gel column, elution being carried out with a mixture of aqueous ammonia, methanol and dichloromethane (2/4/96), to give 0.29 g of a beige solid after crystallization from diisopropyl ether and drying.

Mp: 200-202° C.

$^1$H NMR (DMSO d6) δ: 9.35 (d, 1H); 9.25 (d, 1H); 8.00 (d, 1H); 7.90 (dd, 1H); 7.55 (m, 2H); 7.35 (d, 1H); 7.25 (pseudo t, 2H); 4.45 (t, 1H); 3.4-3.6 (m, 6H); 2.35-2.65 (m, >6H) ppm.

EXAMPLE 9

Compound No. 8: 2-(4-fluorophenyl)-6-(2-fluoroethyl)piperazin-1-yl)-3-(pyridazin-4-yl)imidazo[1,2-b]pyridazine

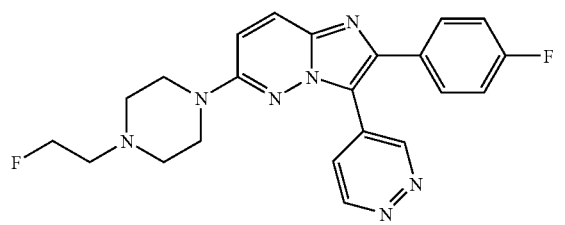 [SMILES: FCCN1CCN(c2ccc3nc(-c4ccc(F)cc4)c(-c4ccnnc4)n3n2)CC1]

The mixture of 0.35 g (1.07 mmol) of 6-chloro-2-(4-fluorophenyl)-3-(pyridazin-4-yl)imidazo[1,2-b]pyridazine, 0.441 g (2.15 mmol) of 2-fluoroethylpiperazine dihydrochloride and 0.75 ml (5.4 mmol) of triethylamine in 4 ml of dimethyl sulfoxide is microwave-heated at 85° C. for 1 hour. The organic phase is dried over sodium sulfate and then concentrated under reduced pressure. The product is chromatographed on a silica gel column, elution being carried out with a mixture of aqueous ammonia, methanol and dichloromethane (0.5/5/95), to give 0.17 g of a brown powder after crystallization from acetonitrile and drying.

Mp: 177-179° C.

$^1$H NMR (DMSO d6) δ: 9.60 (d, 1H); 9.20 (d, 1H); 7.85 (d, 1H); 7.00 (dd, 1H); 7.60 (m, 2H); 7.15 (pseudo t, 2H); 7.00 (d, 1H); 4.75 (m, 1H); 4.60 (m, 1H); 3.6 (m, 4H); 2.85-2.75 (m, 5H) ppm.

EXAMPLE 10

Compound No. 9: 2-phenyl-6-(4-isopropylpiperazin-1-yl)-3-(pyridazin-4-yl)imidazo[1,2-b]pyridazine

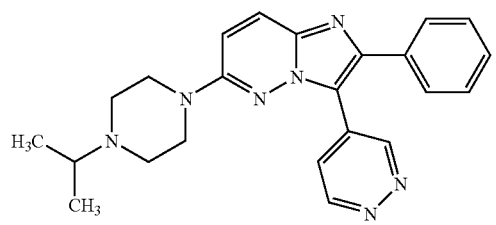 [SMILES: CC(C)N1CCN(c2ccc3nc(-c4ccccc4)c(-c4ccnnc4)n3n2)CC1]

Step 10.1. Ethyl 4-[6-chloro-2-phenylimidazo[1,2-b]pyridazin-3-yl]-4H-pyridazine-1-carboxylate

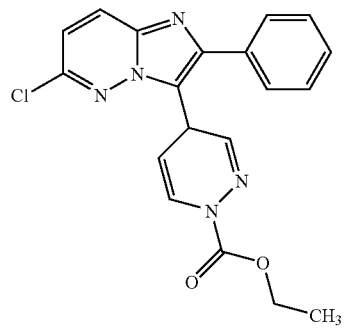 [SMILES: CCOC(=O)N1C=CC(c2c(-c3ccccc3)nc3ccc(Cl)nn23)C=N1]

26.2 ml (30.3 mmol) of ethyl chloroformate are added, dropwise in 30 minutes, to a solution of 25.2 g (109 mmol) of 6-chloro-2-phenylimidazo[1,2-b]pyridazine and 39.8 ml (548 mmol) of pyridazine in 550 ml of dichloromethane at 8° C. The medium is stirred at 10° C. for a further hour and then left to stir for an additional hour. The medium is cooled to 8° C. and 14.9 ml (273 mmol) of pyridazine and 13.1 ml (137 mmol) of ethyl chloroformate are then added in fifteen minutes. The reaction is allowed to return to ambient temperature with stirring for a further hour. The solvent is evaporated off under reduced pressure and the residue is taken up with 1 l of ethyl acetate. The organic phase is washed with a saturated solution of sodium hydrogen carbonate and then with water. The organic phase is dried over sodium sulfate and the solvent is evaporated off under reduced pressure. The product is chromatographed on a neutral alumina column, elution being carried out with a mixture of chloroform and cyclohexane (6/4), to give 35 g of an orangey solid, which is crystallized from 250 ml of diethyl ether, to give 30.1 g of a beige solid.

Mp: 126-131° C.

$^1$H NMR (DMSOd$_6$) δ: 8.30 (d, 1H); 7.4 (d, 1H); 7.4-7.6 (m, 7H); 7.2 (d, 1H); 6.95 (d, 1H); 5.1 (m, 2H); 4.3 (q, 2H); 1.33 (t, 3H) ppm.

Step 10.2. 6-chloro-2-phenyl-3-(pyridazin-4-yl)imidazo[1,2-b]pyridazine

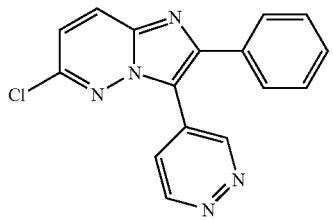 [SMILES: Clc1ccc2nc(-c3ccccc3)c(-c3ccnnc3)n2n1]

22.3 g (58.4 mmol) of ethyl 4-[6-chloro-2-phenylimidazo[1,2-b]pyridazin-3-yl]-4H-pyridazine-1-carboxylate are dissolved in 450 ml of chloroform and 15.1 g (61.3 mmol) of ortho-chloranil are added portionwise. The reaction medium is stirred for 30 minutes at ambient temperature and then poured into a 2N aqueous solution of sodium hydroxide. The product is extracted with chloroform. The organic phase is dried over sodium sulfate and then concentrated under reduced pressure. The dark beige residue is crystallized from a mixture of 80 ml of isopropanol and 60 ml of diisopropyl ether under hot conditions, to give 12.8 g of a beige powder after cooling, isolation by filtration and drying.

Mp: 200-207° C.

$^1$H NMR (CDCl$_3$) δ: 9.40 (s, 1H); 9.30 (d, 1H); 8.05 (d, 1H); 7.90 (m, 1H); 7.65 (m, 2H); 7.45 (m, 3H); 7.25 (m, 1H) ppm.

Step 10.3. 2-phenyl-6-(4-isopropylpiperazin-1-yl)-3-(pyridazin-4-yl)imidazo[1,2-b]pyridazine

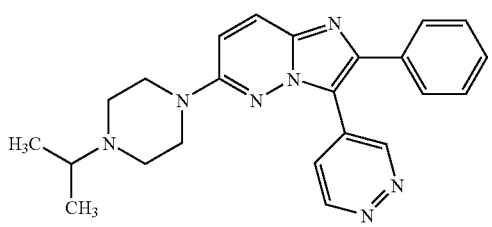 [SMILES: CC(C)N1CCN(c2ccc3nc(-c4ccccc4)c(-c4ccnnc4)n3n2)CC1]

The mixture of 0.45 g (1.5 mmol) of 6-chloro-2-phenyl-3-(pyridazin-4-yl)imidazo[1,2-b]pyridazine and 0.38 g (2.9 mmol) of 1-isopropylpiperazine in 6 ml of pentanol is heated in a sealed tube at 150° C. for 2 days. The mixture is cooled and poured into a 1N aqueous solution of hydrochloric acid. This solution is washed with diethyl ether and then basified using an aqueous solution of sodium hydroxide. The product is finally extracted with dichloromethane, and the organic phase is dried over sodium sulfate, filtered and concentrated under reduced pressure. A brown oil is obtained, which is chromatographed on silica gel, elution being carried out with a mixture of aqueous ammonia, methanol and dichloromethane (0.4/4/96), to give 0.50 g of a solid.

The latter is recrystallized from 30 ml of diethyl ether. 0.29 g of a white solid is finally isolated after filtration and drying.

Mp: 154-156° C.

$^1$H NMR (DMSO d6) δ: 9.35 (d, 1H); 9.30 (d, 1H); 8.05 (d, 1H); 7.95 (dd, 1H); 7.60 (m, 2H); 7.4 (m, 4H); 3.50 (m, 4H); 2.70 (m, 1H); 2.60 (m, 4H); 1.00 (d, 6H) ppm.

EXAMPLE 11

Compound No. 18: 2-(4-fluorophenyl)-6-(4-cyclopropylpiperazin-1-yl)-3-(pyridazin-4-yl)imidazo[1,2-b]pyridazine

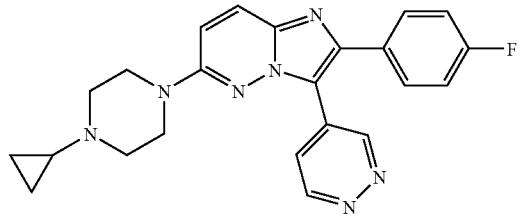 [SMILES: Fc1ccc(-c2nc3ccc(N4CCN(C5CC5)CC4)nn3c2-c2ccnnc2)cc1]

0.15 ml of acetic acid and 0.32 ml (1.6 mmol) of (1-ethoxycyclopropoxy)trimethylsilane are added, in a reactor, to 0.10 g (0.27 mmol) of 2-(4-fluorophenyl)-6-(piperazin-1-yl)-3-(pyridazin-4-yl)imidazo[1,2-b]pyridazine in 3 ml of methanol. 1.2 ml (1.2 mmol) of a molar solution of sodium cyanoborohydride in tetrahydrofuran are then added. After stirring for 15 minutes, the mixture is heated at 50° C. for 2 hours. After cooling, the product is extracted with dichloromethane, and the organic phase is filtered over a hydrophobic cartridge and then concentrated under reduced pressure. The residue is chromatographed on a silica gel column, to give 0.064 g of product. The latter is crystallized from diisopropyl ether, to give 0.053 g of light yellow crystals after drying.

Mp: 206-209° C.

$^1$H NMR (DMSO d6) δ: 9.35 (s, 1H); 9.30 (d, 1H); 8.05 (d, 1H); 7.90 (dd, 1H); 7.60 (m, 2H); 7.40 (d, 1H); 7.25 (pseudo t, 2H); 3.45 (m, 4H); 2.70 (m, 4H); 1.70 (m, 1H); 0.45 (m, 2H); 0.35 (m, 2H) ppm.

EXAMPLE 12

Compound No. 36: 2-(3,5-difluorophenyl)-3-(pyridazin-4-yl)-6-(4-pyrrolidin-1-yl-piperidin-1-yl)imidazo[1,2-b]pyridazine

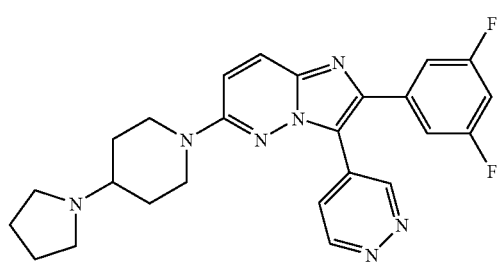 [SMILES: Fc1cc(F)cc(-c2nc3ccc(N4CCC(N5CCCC5)CC4)nn3c2-c2ccnnc2)c1]

Step 12.1. 6-amino-3-chloro-1-(ethoxycarbonylmethyl)pyridazin-1-ium bromide

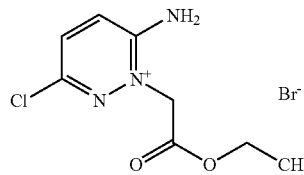

A mixture of 25.6 g (198 mmol) of 6-chloro-2-phenylimidazo[1,2-b]pyridazine in 230 ml of hot ethanol is treated with 34.0 g (206 mmol) of ethyl bromoacetate. After refluxing for 24 hours, the mixture is cooled and the crystals are separated by filtration.

36.6 g of product are isolated after drying.

A further 7.1 g are isolated by evaporation of the solvent under reduced pressure and recrystallization from ethanol.

$^1$H NMR (DMSO d6) δ: 9.8 (broad signal, 1H); 9.4 (broad signal, 1H); 8.0 (d, 1H); 7.7 (d, 1H); 5.3 (s, 1H); 4.1 (d, 2H); 1.2 (t, 3H) ppm.

Step 12.2. 2-bromo-6-chloroimidazo[1,2-b]pyridazine and 2,6-dibromoimidazo[1,2-b]pyridazine

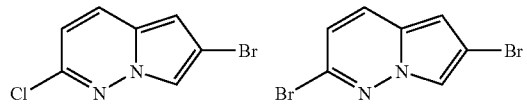 [SMILES: Clc1ccc2cc(Br)cn2n1 ; Brc1cc2ccc(Br)nn2c1]

The mixture of 20 g (65 mmol) of 6-amino-3-chloro-1-(ethoxycarbonylmethyl)pyridazin-1-ium bromide and 63 g of phosphorus oxybromide in 50 ml of toluene is heated at 160° C. for 3 hours. The mixture is then poured onto ice (300 ml). After stirring, the solid is separated by filtration and then purified by silica gel chromatography, elution being carried out with a mixture of 0 to 10% of methanol in dichloromethane. 8.05 g of mixture of the two products are thus obtained, and used without further modification for the rest of the synthesis.

Step 12.3. 2-bromo-6-(4-pyrrolidin-1-ylpiperidin-1-yl)imidazo[1,2-b]pyridazine

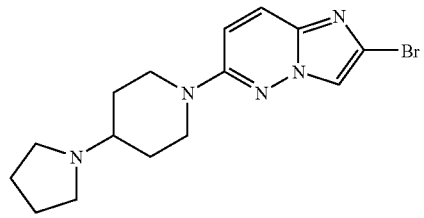 [SMILES: Brc1cn2nc(N3CCC(N4CCCC4)CC3)ccc2n1]

1.42 g (5.1 mmol) of the mixture obtained in the preceding step and 2.42 g (15.7 mmol) of 4-pyrrolidin-1-ylpiperidine in 15 ml of butanol are microwave-heated at 180° C. for 5 hours in a sealed tube. The solvent is then eliminated by evaporation under reduced pressure and the residue is chromatographed on a silica gel column, elution being carried out with a mixture of 0 to 10% of methanol in dichloromethane. 1.58 g of product are thus isolated.

$^1$H NMR (CDCl$_3$) δ: 7.6 (d+s, 2H); 6.8 (d, 1H); 4.05 (m, 2H); 3.0 (m, 2H); 2.6 (m, 4H); 2.2 (m, 1H); 2.0 (m, 2H); 1.8 (m, 4H); 1.6 (m, 2H) ppm.

Step 12.4. ethyl 4-[2-bromo-6-(4-pyrrolidin-1-ylpiperidin-1-yl)imidazo[1,2-b]pyridazin-3-yl]-4H-pyridazine-1-carboxylate

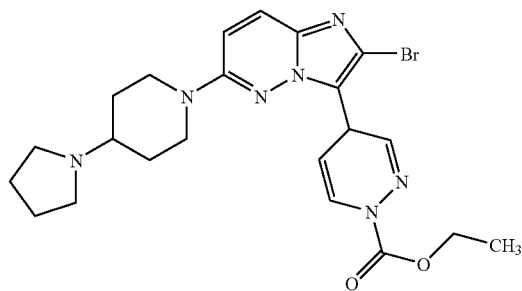 [SMILES: CCOC(=O)N1C=CC(c2c(Br)nc3ccc(N4CCC(N5CCCC5)CC4)nn23)C=N1]

1.3 g (12 mmol) of ethyl chloroformate are added, dropwise in 5 minutes, while cooling in an ice bath, to a mixture of 1.68 g (4.8 mmol) of 2-bromo-6-(4-pyrrolidin-1-ylpiperidin-1-yl)imidazo[1,2-b]pyridazine and 1.92 g (24 mmol) of pyridazine in 25 ml of chloroform. The mixture is stirred at ambient temperature for one hour and is then diluted with dichloromethane, and the solution is washed successively with a solution of sodium bicarbonate and then with a saturated solution of sodium chloride. The organic phase is dried over sodium sulfate and then concentrated under reduced pressure after the addition of silica gel. The evaporation residue is loaded onto a silica gel column and the product is purified by silica gel column chromatography, elution being carried out with a mixture of 0 to 10% of methanol in dichloromethane. 1.93 g of product sufficiently pure for the rest of the synthesis are thus isolated.

$^1$H NMR (CDCl$_3$) δ: 7.5 (d, 1H); 7.3 (m); 6.8 (m, 2H); 4.8 (m, 1H); 4.7 (m, 1H); 4.3 (q, 2H); 3.95 (m, 2H); 2.9 (m, 2H); 2.5 (m, 4H); 2.2 (m, 1H); 1.9 (m, 2H); 1.8 (m, 4H); 1.5 (m, 4H); 1.3 (t, 3H) ppm.

Step 12.5. 2-bromo-3-pyridazin-4-yl-6-(4-pyrrolidin-1-ylpiperidin-1-yl)imidazo[1,2-b]pyridazine

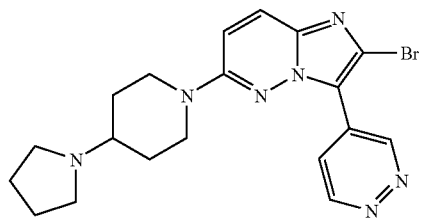 [SMILES: Brc1nc2ccc(N3CCC(N4CCCC4)CC3)nn2c1-c1ccnnc1]

0.101 g of ortho-chloranil (0.41 mmol) in solution in 1 ml of toluene is added to a mixture of 0.16 g (0.32 mmol) of ethyl 4-[2-bromo-6-(4-pyrrolidin-1-ylpiperidin-1-yl)imidazo[1,2-b]pyridazin-3-yl]-4H-pyridazine-1-carboxylate in 4 ml of chloroform. The mixture is stirred at ambient temperature for 1 hour and then diluted with 40 ml of dichloromethane. The solution is washed with 2 ml of a 2N aqueous solution of sodium hydroxide and then with a saturated solution of sodium chloride. The organic phase is dried over sodium sulfate and then concentrated under reduced pressure after the addition of silica gel. The evaporation residue is loaded onto a silica gel column and the product is purified by chromatography on a silica gel column, elution being carried out with a mixture of 0 to 10% of methanol in dichloromethane. 0.080 g of product is thus isolated.

$^1$H NMR (CDCl$_3$) δ: 9.95 (d, 1H); 9.29 (d, 1H); 8.15 (dd, 1H); 7.60 (d, 1H); 6.85 (d, 1H); 4.1 (m, 2H); 3.7 (m, 2H); 2.7 (m, 4H); 2.3 (m, 1H); 2.0 (m, 2H); 1.8 (m, 4H); 1.7 (m, 2H) ppm.

Step 12.6. 2-(3,5-difluorophenyl)-3-(pyridazin-4-yl)-6-(4-pyrrolidin-1-ylpiperidin-1-yl)imidazo[1,2-b]pyridazine A mixture of 0.090 g (0.21 mmol) of 2-bromo-3-pyridazin-4-yl-6-(4-pyrrolidin-1-ylpiperidin-1-yl)imidazo[1,2-b]pyridazine, 0.014 g (0.02 mmol) of 1,1'-bis(diphenylphosphino)ferrocenedichloropalladium and 0.043 g (0.27 mmol) of 3,5-difluorophenylboronic acid and of a 2M aqueous solution of cesium carbonate in 2 ml of dioxane is heated at 120° C. for 20 minutes in a microwave oven. 1 ml of a saturated aqueous solution of sodium chloride and 4 ml of ethyl acetate are then injected into the tube. After stirring, the organic phase is removed with a syringe and passed over a sodium sulfate cartridge. The solution is directly injected onto a silica gel column and chromatographed, elution being carried out with a mixture of 0 to 10% of methanol in dichloromethane. 0.037 g of product is thus isolated.

$^1$H NMR (CDCl$_3$) δ: 9.6 (m, 1H); 9.2 (d, 1H); 7.8 (m, 2H); 7.2 (m, 2H); 7.05 (d, 1H); 6.9 (m, 1H); 4.10 (m, 2H); 3.1 (m, 2H); 2.7 (m, 4H); 2.35 (m, 1H); 2.1 (m, 2H); 1.9 (m, 4H); 1.7 (m, 2H) ppm.

Table 1 which follows illustrates the chemical structures and the physical properties of a number of compounds according to the invention.

In this table:
- the "m.p. ° C." column gives the melting points of the products in degrees Celsius.
- "N.D." means that the melting point is not determined,
- the "LC-MS or (MS)" column gives an analysis of the products by LC-MS (liquid chromatography coupled to mass spectroscopy) performed on an Agilent LC-MSD Trap machine in positive ESI mode or by MS (mass spectroscopy) on an Autospec M machine (EBE) using the DCl—NH$_3$ technique,
- "CH$_3$" means methyl.

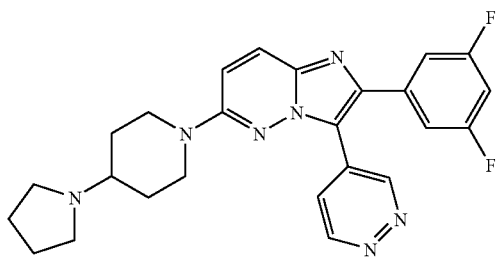 [SMILES: Fc1cc(F)cc(-c2nc3ccc(N4CCC(N5CCCC5)CC4)nn3c2-c2ccnnc2)c1]

TABLE 1

| No. | -N-A-L-B- | R$_7$ | R$_8$ | R$_2$ | m.p. ° C. | M + H |
|---|---|---|---|---|---|---|
| 1 | Piperazin-1-yl | H | H | 4-Fluorophenyl | 240-246 | 376 |
| 2 | 3-(R)-Methylpiperazin-1-yl | H | H | 4-Fluorophenyl | 162-164 | 390 |
| 3 | 3,3-Dimethylpiperazin-1-yl | H | H | 4-Fluorophenyl | 226-228 | 404 |
| 4 | cis-3,5-Dimethylpiperazin-1-yl | H | H | 4-Fluorophenyl | 197-199 | 404 |
| 5 | 4-Methylpiperazin-1-yl | H | H | 4-Fluorophenyl | 232-233 | 390 |
| 6 | 4-(2-Hydroxyethyl)piperazin-1-yl | H | H | 4-Fluorophenyl | 200-202 | 420 |
| 7 | 4-(2-Fluoroethyl)piperazin-1-yl | H | H | Phenyl | 156-158 | 404 |
| 8 | 4-(2-Fluoroethyl)piperazin-1-yl | H | H | 4-Fluorophenyl | 177-179 | 422 |
| 9 | 4-Isopropylpiperazin-1-yl | H | H | Phenyl | 154-156 | 400 |
| 10 | 4-Isopropylpiperazin-1-yl | H | H | 3-Fluorophenyl | 197-199 | 418 |
| 11 | 4-Isopropylpiperazin-1-yl | H | H | 4-Fluorophenyl | 172-174 | 418 |
| 12 | 4-Isopropylpiperazin-1-yl | CH$_3$— | CH$_3$— | 4-Fluorophenyl | 222-224 | 446 |
| 13 | 4-Isopropylpiperazin-1-yl | H | H | 3,5-Dimethylphenyl | 183-184 | 428 |
| 14 | 4-Isopropylpiperazin-1-yl | H | H | 3,4-Difluorophenyl | 192-194 | 436 |
| 15 | 4-Isopropylpiperazin-1-yl | H | H | 3,5-Difluorophenyl | N.D. | 436 |
| 16 | 4-Isopropylpiperazin-1-yl | H | H | 3,5-Dichlorophenyl | N.D. | 468 |
| 17 | 4-Isopropylpiperazin-1-yl | H | H | 3,5-Di(trifluoromethyl)phenyl | N.D. | 536 |
| 18 | 4-Cyclopropylpiperazin-1-yl | H | H | 4-Fluorophenyl | 206-209 | 416 |
| 19 | 4-Benzylpiperazin-1-yl | H | H | 4-Fluorophenyl | 198-201 | 466 |
| 20 | 4-(2-Hydroxy-2-methylpropyl)piperazin-1-yl | H | H | 4-Fluorophenyl | 200-202 | 448 |
| 21 | 4-(3-Hydroxy-3-methylbutyl)piperazin-1-yl | H | H | 4-Fluorophenyl | 148-150 | 462 |
| 22 | (S)-Octahydropyrrolo[1,2-a]pyrazin-2-yl 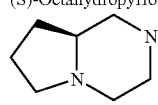 | H | H | 4-Fluorophenyl | 203-205 | 416 |
| 23 | (1S,4S)-2,5-Diazabicyclo[2.2.1]hept-2-yl  | H | H | 4-Fluorophenyl | 205-207 | 388 |

TABLE 1-continued

| No. | -N-A-L-B- | $R_7$ | $R_8$ | $R_2$ | m.p. ° C. | M + H |
|---|---|---|---|---|---|---|
| 24 | 5-(2-Hydroxyethyl)-(1S,4S)-2,5-diaza-bicyclo[2.2.1]hept-2-yl | H | H | 4-Fluorophenyl | 175-177 | 432 |
| 25 | 5-Isopropyl-(1S,4S)-2,5-diaza-bicyclo[2.2.1]hept-2-yl | H | H | 4-Fluorophenyl | 201-203 | 430 |
| 26 | Hexahydro-pyrrolo[3,4-c]pyrrol-2-(1H)-yl | H | H | 4-Fluorophenyl | 130-135 | 402 |
| 27 | 5-Methylhexahydropyrrolo[3,4-c]pyrrol-2-(1H)-yl | H | H | 4-Fluorophenyl | 150-152 | 416 |
| 28 | 5-(2-Isopropyl)hexahydropyrrolo[3,4-c]pyrrol-2-(1H)-yl | H | H | 4-Fluorophenyl | 198-200 | 444 |
| 29 | 5-(2-Hydroxyethyl)hexahydropyrrolo[3,4-c]pyrrol-2-(1H)-yl | H | H | 4-Fluorophenyl | 208-210 | 446 |
| 30 | 5-(Benzyl)hexahydropyrrolo[3,4-c]pyrrol-2-(1H)-yl | H | H | 4-Fluorophenyl | N.D. | 492 |
| 31 | 2,9-Diazaspiro[5.5]undec-9-yl | H | H | 4-Fluorophenyl | 203-205 | 444 |
| 32 | 1-Oxa-4,9-diazaspiro[5.5]undec-9-yl | H | H | 4-Fluorophenyl | 212-214 | 446 |
| 33 | (R,S)-3-[Pyrrolidin-1-yl]pyrrolidin-1-yl- | H | H | 4-Fluorophenyl | 182-184 | 430 |
| 34 | 4-(Pyrrolidin-1-yl)piperidin-1-yl | H | H | 4-Fluorophenyl | 196-198 | 444 |
| 35 | 4-(Pyrrolidin-1-yl)piperidin-1-yl | H | H | 3,5-Dimethylphenyl | N.D. | 454 |
| 36 | 4-(Pyrrolidin-1-yl)piperidin-1-yl | H | H | 3,5-Difluorophenyl | N.D. | 426 |
| 37 | 4-(Pyrrolidin-1-yl)piperidin-1-yl | H | H | 3,5-Dichlorophenyl | N.D. | 494 |
| 38 | 4-(Pyrrolidin-1-yl)piperidin-1-yl | H | H | 3,5-Di(trifluoromethyl)phenyl | N.D. | 526 |
| 39 | 3-(Hydroxymethyl)piperazin-1-yl | H | H | 4-Fluorophenyl | 205-212 | 406 |
| 40 | 3-(Fluoromethyl)piperazin-1-yl | H | H | 4-Fluorophenyl | 184-189 | 408 |
| 41 | 5-Methylhexahydropyrrolo[3,4-c]pyrrol-2-(1H)-yl | H | H | Phenyl | 154-157 | 398 |
| 42 | 5-Methylhexahydropyrrolo[3,4-c]pyrrol-2-(1H)-yl | H | H | 3-Fluorophenyl | 168-170 | 416 |
| 43 | 5-Methylhexahydropyrrolo[3,4-c]pyrrol-2-(1H)-yl | CH$_3$— | H | 4-Fluorophenyl | 187-189 | 430 |
| 44 | 5-Methylhexahydropyrrolo[3,4-c]pyrrol-2-(1H)-yl | H | CH$_3$— | 4-Fluorophenyl | 255-257 | 430 |
| 45 | 5-Methylhexahydropyrrolo[3,4-c]pyrrol-2-(1H)-yl | H | H | 3,4-Difluorophenyl | 186-188 | 434 |

BIOLOGICAL EXAMPLES

The capacity of the compounds of the invention to inhibit the phosphorylation of casein by casein kinase 1 epsilon and delta may be evaluated according to the procedure described in US 2005/0131012.

Filter-Plate Assay of ATP-$^{33}$P for the Screening of CK1 Epsilon Inhibitors:

The effect of the compounds on inhibition of the phosphorylation of casein by the enzyme casein kinase 1 epsilon (CK1 epsilon) is measured, using a casein assay with filtration of ATP-$^{33}$P in vitro.

Casein kinase 1 epsilon (0.58 mg/ml) is obtained via fermentation and purification processes performed according to methods that are well known to those skilled in the art, or may also be obtained from Invitrogen Corporation™ (human CK1 epsilon).

The compounds are tested at five different concentrations so as to generate IC$_{50}$ values, i.e. the concentration at which a compound is capable of inhibiting the enzymatic activity by 50%, or alternatively the percentage of inhibition at a concentration of 10 micromolar.

"U"-bottomed Falcon plates are prepared by placing 5 μL of solutions of the compounds according to the invention at concentrations of 10, 1, 0.1, 0.01 or 0.001 μM in various wells. The solutions of the compounds according to the invention at these various concentrations are prepared by diluting in a test buffer (50 mM Tris, pH 7.5, 10 M MgCl$_2$, 2 mM DTT and 1 mM EGTA) a stock solution in DMSO at a concentration of 10 mM. Next, 5 µL of dephosphorylated casein are added to a final concentration of 0.2 µg/µL, 20 µl of CK1 epsilon to a final concentration of 3 ng/µl, and 20 µl of ATP-$^{33}$P to a final concentration of 0.02 µCi/µl mixed with cold ATP (10 µM final—approximately $2\times10^6$ CPM per well). The final total test volume per well is equal to 50 µl.

The "U"-bottomed Falcon® test plate mentioned above is vortexed, and then incubated at ambient temperature for 2 hours. After 2 hours, the reaction is stopped by adding an ice-cold solution of 65 µl of ATP (2 mM) prepared in test buffer.

100 µl of the reaction mixture are then transferred from the "U"-bottomed Falcon® plate into Millipore® MAPH filter plates, preimpregnated with 25 µl of ice-cold 100% TCA.

The Millipore MAPH filter plates are agitated gently and are left to stand at ambient temperature for at least 30 minutes to precipitate the proteins. After 30 minutes, the filter plates are sequentially washed and filtered with $2\times150$ µl of 20% TCA, $2\times150$ µl of 10% TCA and $2\times150$ µl of 5% TCA (6 washes in total per plate/900 µl per well).

The plates are left to dry overnight at ambient temperature. Next, 40 µl of Microscint-20 Packard® scintillation liquid are added per well and the plates are closed in a leaktight manner. The radiation emitted by each well is then measured for 2 minutes in a Packard® Topcount NXT scintillation counter, in which the values of CPM/well are measured.

The percentage inhibition of the capacity of the enzyme to phosphorylate the substrate (casein) is determined for each concentration of compound tested. These inhibition data expressed as percentages are used to calculate the $IC_{50}$ value for each compound compared with the controls.

The kinetic studies determined the $K_M$ value for ATP as being 21 µM in this test system.

Table 2 below gives the $IC_{50}$ values for the inhibition of phosphorylation of casein kinase 1 epsilon for a number of compounds according to the invention.

TABLE 2

| Compound No. | CK1 epsilon $IC_{50}$ (nM) |
| --- | --- |
| 5 | 16-33 |
| 21 | 134-166 |
| 28 | 54-69 |
| 39 | 98 |

Under these conditions, the most active compounds of the invention show $IC_{50}$ values (concentration which inhibits 50% of the enzymatic activity of casein kinase 1 epsilon) of between 1 nM and 2 µM.

The capacity of the compounds of the invention to inhibit the phosphorylation of casein by casein kinase 1 epsilon and delta may be evaluated using a FRET ("Fluorescence Resonance Energy Transfer) fluorescence test with the aid of the "Z'Lyte™ kinase assay Kit" (reference PV3670; Invitrogen Corporation™) according to the manufacturer's instructions.

The casein kinases 1 used are obtained from Invitrogen Corporation (human CK1 epsilon PV3500 and human CK1 delta PV3665).

A peptide substrate, labeled at both ends with a fluorophore donor group (coumarin) and a fluorophore acceptor group (fluorescence) constituting a FRET system is phosphorylated in the presence of ATP by casein kinase 1 epsilon or delta in the presence increasing concentrations of compounds of the invention. The mixture is treated with a site-specific protease that specifically cleaves the peptide substrate to form two fluorescent fragments having a large fluorescence emission ratio.

The fluorescence observed is thus related to the capacity of the products of the invention to inhibit the phosphorylation of the peptide substrate by casein kinase 1 epsilon or casein kinase 1 delta.

The compounds of the invention are dissolved at different concentrations starting with a 10 mM stock solution in DMSO diluted in a buffer containing 50 mM HEPS, pH 7.5, 1 m MEGTA, 0.01% Brij-35, 10 mM MgCl for casein kinase 1 epsilon and supplemented with Trizma Base (50 mM), pH 8.0, and $NaN_3$ (0.01% final) for casein kinase 1 delta.

The phosphorylation of the peptide substrate SER/THR 11 obtained from Invitrogen Corporation™ is performed at a final concentration of 2 µM. The ATP concentration is 4 times the $K_M$, this value being 2 µM for casein kinase 1 epsilon and 4 µM for casein kinase 1 delta.

The emitted fluorescence is measured at wavelengths of 445 and 520 nm (excitation at 400 nm).

Table 3 below gives the $IC_{50}$ values for the inhibition of phosphorylation of casein kinase 1 delta for a number of compounds according to the invention.

TABLE 3

| Compound No. | CK1 delta $IC_{50}$ (nM) |
| --- | --- |
| 1 | 1 |
| 5 | 41-56 |
| 11 | 50-65 |

Under these conditions, the compounds of the invention that are the most active have $IC_{50}$ values (concentration that inhibits 50% of the enzymatic activity of casein kinase 1 delta) of between 1 nM and 2 µM.

It is thus seen that the compounds according to the invention have inhibitory activity on the casein kinase 1 epsilon or casein kinase 1 delta enzyme.

Experimental Protocols for Circadian Cell Assay

Mper1-luc Rat-1 (P2C4) fibroblast cultures were prepared by dividing the cultures every 3-4 days (approximately 10-20% of confluence) on 150 $cm^2$ degassed polystyrene tissue culture flasks (Falcon® #35-5001) and maintained in growth medium [EMEM (Cellgro #10-010-CV); 10% fetal bovine serum (FBS; Gibco #16000-044); and 50 I.U./ml of penicillin-streptomycin (Cellgro #30-001-CI)] at 37° C. and under 5% $CO_2$.

Cells obtained from Rat-1 fibroblast cultures at 30-50% of confluence as described above were co-transfected with vectors containing the selection marker for resistance to zeocin for a stable transfection and a luciferase reporter gene controlled by the mPer-1 promoter. After 24 to 48 hours, the cultures were divided on 96-well plates and maintained in growth medium supplemented with 50-100 µg/ml of zeocin (Invitrogen® #45-0430) for 10-14 days. The zeocin-resistant stable transfectants were evaluated for the expression of the reporter by adding 100 µM lucerfin (Promega® #E1603®) to the growth medium and by assaying the luciferase activity on a TopCount® scintillation counter (Packard Model #C384V00). The Rat-1 cell clones expressing both zeocin resistance and lucerifase activity controlled by mPer1 were serum-shock synchronized with 50% horse serum [HS (Gibco® #16050-122)] and the activity of the circadian reporter was evaluated. The P2C4 clone of Mper1-luc Rat-1 fibroblasts was selected to test the compound.

Mper1-luc Rat-1 (P2C4) fibroblasts at 40-50% of confluence, obtained according to the protocol described above, were plated out onto 96-well opaque tissue culture plates (Perkin Elmer® #6005680). The cultures are maintained in growth medium supplemented with 100 µg/ml of zeocin (Invitrogen #45-0430) until they reach 100% of confluence (48-72 h). The cultures were then synchronized with 100 µl of synchronization medium [EMEM (Cellgro #10-010-CV); 100 I.U./ml of penicillin-streptomycin (Cellgro #30-001-C1); 50% HS (Gibco #16050-122)] for 2 hours at 37° C. and under 5% $CO_2$. After synchronization, the cultures were rinsed with 100 µl of EMEM (Cellgro #10-010-CV) for 10 minutes at ambient temperature. After rinsing, the medium was replaced with 300 µl of $CO_2$ independent medium [$CO_2$I (Gibco #18045-088); 2 mM L-glutamine (Cellgro #25-005-C1); 100 U.I./ml of penicillin-streptomycin (Cellgro #30-001-C1); 100 µM luciferin (Promega #E 1603)]. The compounds of the invention tested for the circadian effects were added to $CO_2$-independent medium in DMSO at 0.3% (final concentration). The cultures were immediately closed in a leaktight manner with TopSeal-A® film (Packard #6005185) and transferred for the luciferase activity measurement. After synchronization, the test plates were maintained at 37° C. in a tissue culture incubator (Form a Scientific Model #3914). The in vivo lucerifase activity was estimated by measuring the relative light emission on a TopCount scintillation counter (Packard Model #C384V00).

The period analysis was performed either by determining the interval between the relative light emission minima over several days or by Fourier transform. The two methods produced a virtually identical period estimation on a range of circadian periods. The power is reported in CE Delta (t+1 h), which is presented as the effective micromolar concentration that induced a 1-hour prolongation of the period. The data were analyzed by adjusting a hyperbolic curve to the data expressed as change of period (y-axis) as a function of the concentration of the test compound (x-axis) in the XLfit™ software and the CE Delta (t+1 h) was interpolated from this curve.

Table 4 below gives the CE Delta (t+1 h) for a number of compounds according to the invention.

TABLE 4

| Compound No. | CE Delta (t + 1 h) (nM) |
|---|---|
| 2 | 164 |
| 5 | 5 |
| 14 | 62 |
| 39 | 178 |

Under these conditions, the compounds of the invention that are the most active have CE Delta (t+1 h) values (effective micromolar concentration that induced a 1-hour prolongation of the period) of between 1 nM and 2 µM.

By inhibiting the enzymes CK1epsilon and/or CK1delta, the compounds that are the subjects of the invention modulate the circadian periodicity, and may be useful for treating circadian rhythm disorders.

The compounds according to the invention may in particular be used for the preparation of a medicament for preventing or treating sleep disorders: circadian rhythm disorders, such as, in particular, those caused by jetlag or shift work. Among the sleep disorders that are especially distinguished are primary sleep disorders such as dyssomnia (for example primary insomnia), parasomnia, hypersomnia (for example excessive somnolence), narcolepsy, sleep disorders related to sleep apnea, sleep disorders related to the circadian rhythm and otherwise unspecified dyssomnias, sleep disorders associated with medical/psychiatric disorders.

The compounds that are the subjects of the invention also cause a circadian phase shift and such a property may be useful in the context of a potential monotherapy or combined therapy that is clinically effective in the case of mood disorders. Among the mood disorders that are especially distinguished are depressive disorders (unipolar depression), bipolar disorders, mood disorders caused by a general medical complaint and also mood disorders induced by pharmacological substances.

Among the bipolar disorders that are especially distinguished are bipolar I disorders and bipolar II disorders, including in particular seasonal affective disorders.

The compounds that are the subjects of the invention, which modulate the circadian periodicity, may be useful in the treatment of anxiety and depressive disorders caused in particular by an impairment in the secretion of CRF.

Among the depressive disorders that are especially distinguished are major depressive disorders, dysthymic disorders and otherwise unspecified depressive disorders.

The compounds that are the subjects of the invention, which modulate the circadian periodicity, may be useful for preparing a medicament for treating diseases related to dependency on abuse substances such as cocaine, morphine, nicotine, ethanol or cannabis.

By inhibiting casein kinase 1 epsilon and/or casein kinase 1 delta, the compounds according to the invention may be used for preparing medicaments, in particular for preparing a medicament for preventing or treating diseases related to hyperphosphorylation of the tau protein, in particular Alzheimer's disease.

These medicaments also find their use in therapy, in particular in the treatment or prevention of diseases caused or exacerbated by the proliferation of cells, in particular tumor cells.

As tumor cell proliferation inhibitors, these compounds are useful in the prevention and treatment of liquid tumors such as leukaemias, solid tumors that are both primary and metastatic, carcinomas and cancers, in particular: breast cancer, lung cancer, small intestine cancer, colorectal cancer; cancer of the respiratory pathways, of the oropharynx and of the hypopharynx; esophageal cancer; liver cancer, stomach cancer, cancer of the bial ducts, cancer of the gall bladder, pancreatic cancer; cancer of the urinary tracts, including kidney, urothelium and bladder; cancers of the female genital tract, including cancer of uterus, cervical cancer, ovarian cancer, chloriocarcinomia and trophoblastomia; cancers of the male genital tract, including prostate cancer, cancer of the seminal vesicles, testicular cancer and germinal cell tumors; cancers of the endocrine glands, including thyroid cancer, pituitary cancer and cancer of the adrenal glands; skin cancers, including haemangiomas, melanomas and sarcomas, including Kaposi's sarcoma; brain, nerve, eye or meninges tumors, including astrocytomas, gliomas, glioblastomas, retinoblastomas, neurinomas, neuroblastomas, schwannomas and meningiomas; malignant hematopoietic tumors; leukaemias (Acute Lymphocytic Leukemia (ALL), Acute Myeloid Leukemia (AML), Chronic Myeloid Leukemia (CML), Chronic Lymphocytic Leukemia (CLL)), chloromas, plasmocytomas, T or B cell leukaemias, Hodgkin or non-Hodgkin lymphomas, myelomas and various malignant haemopathies.

The compounds according to the invention may thus be used for the preparation of medicaments, in particular of medicaments for inhibiting casein kinase 1 epsilon and/or casein kinase 1 delta.

Thus, according to another of its aspects, a subject of the invention is medicaments which comprise a compound of formula (I), or an addition salt thereof with a pharmaceutically acceptable acid, or alternatively a hydrate or a solvate of the compound of formula (I).

According to another of its aspects, the present invention relates to pharmaceutical compositions comprising, as active principle, a compound according to the invention. These pharmaceutical compositions contain an effective dose of at least one compound according to the invention or a pharmaceutically acceptable salt, a hydrate or a solvate of said compound, and also at least one pharmaceutically acceptable excipient.

Said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in unit administration form, as a mixture with standard pharmaceutical excipients, to humans and animals for the prophylaxis or treatment of the above disorders or diseases.

The appropriate unit administration forms include oral-route forms such as tablets, soft or hard gel capsules, powders, granules and oral solutions or suspensions, sublingual, buccal, intratracheal, intraocular and intranasal administration forms, inhalation forms, topical, transdermal, subcutaneous, intramuscular or intravenous administration forms, rectal administration forms and implants. For topical application, the compounds according to the invention may be used in creams, gels, ointments or lotions.

By way of example, unit administration form of a compound according to the invention, in tablet form may comprise the following components:

| | |
|---|---|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may reach from 0.1 to 20 mg/kg, in one or more dosage intakes.

There may be particular cases in which higher or lower dosages are appropriate; such dosages do not depart from the context of the invention. According to the usual practice, the dosage that is appropriate to each patient is determined by the practitioner according to the mode of administration and the weight and response of said patient.

According to another of its aspects, the present invention also relates to a method for treating the pathologies indicated above, which comprises the administration to a patient of an effective dose of a compound according to the invention, or a pharmaceutically acceptable salt or hydrate or solvate thereof.

What is claimed is:
1. A compound of formula (I):

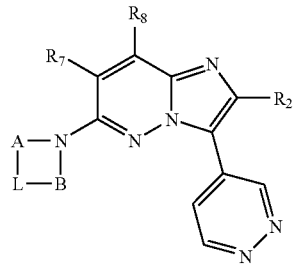

in which:
$R_2$ represents an aryl group optionally substituted with one or more substituents chosen from halogen atoms and the groups $C_{1-6}$ alkyl, $C_{1-6}$ alkyloxy, $C_{1-6}$ alkylthio, $C_{1-6}$ fluoroalkyl, $C_{1-6}$-fluoroalkyloxy and —CN;

A represents a group $C_{1-7}$-alkylene optionally substituted with one or two groups $R_a$;

B represents a group $C_{1-7}$-alkylene optionally substituted with a group $R_b$;

L represents either a nitrogen atom substituted with a group $R_c$ or $R_d$, or a carbon atom substituted with a group $R_{e1}$ and a group $R_d$ or two groups $R_{e2}$;

the carbon atoms of A and B being optionally substituted with one or more groups $R_f$, which may be identical to or different from one another;

$R_a$, $R_b$ and $R_c$ are defined such that:
two groups $R_a$ may together form a group $C_{1-6}$-alkylene;
$R_a$ and $R_b$ may together form a bond or a group $C_{1-6}$-alkylene;
$R_a$ and $R_c$ may together form a bond or a group $C_{1-6}$-alkylene;
$R_b$ and $R_c$ may together form a bond or a group $C_{1-6}$-alkylene;

$R_d$ represents a group chosen from a hydrogen atom and the groups $C_{1-6}$-alkyl, $C_{3-7}$-cycloalkyl, $C_{3-7}$-cycloalkyl-$C_{1-6}$ alkyl, hydroxy-$C_{1-6}$-alkyl, $C_{1-6}$-alkyloxy-$C_{1-6}$-alkyl, $C_{1-6}$-alkylthio-$C_{1-6}$-alkyl, $C_{1-6}$-fluoroalkyl and benzyl;

$R_{e1}$ represents a group —$NR_4R_5$ or a cyclic monoamine which is pyrrolidinyl optionally substituted with one or more substituents chosen from a fluorine atom and the groups $C_{1-6}$-alkyl, $C_{1-6}$-alkyloxy and hydroxyl;

two groups $R_{e2}$ form, with the carbon atom that bears them, a cyclic monoamine optionally having an oxygen ring atom thereon selected from azetidine, pyrrolidine, piperidine and morpholine group, this cyclic monoamine being optionally substituted with one or more groups $R_f$, which may be identical to or different from one another;

$R_f$ represents a group $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl or benzyl;

$R_4$ and $R_5$ represent, independently of each other, a hydrogen atom or a group $C_{1-6}$-alkyl, $C_{3-7}$-cycloalkyl or $C_{3-7}$-cycloalkyl-$C_{1-6}$-alkyl; and $R_7$ and $R_8$ represent, independently of each other, a hydrogen atom or a group $C_{1-6}$-alkyl;

or a salt thereof.

2. The compound of formula (I) according to claim 1, wherein $R_2$ represents a phenyl optionally substituted with one or more halogen atoms or groups $C_{1-6}$ alkyl or $C_{1-6}$ fluoroalkyl.

3. The compound of formula (I) according to claim 1, wherein $R_2$ represents a phenyl, 3-fluorophenyl, 4-fluorophenyl, 3,4-difluorophenyl, 3,5-difluorophenyl, 3,5-dichlorophenyl, 3,5-dimethylphenyl or 3,5-di(trifluoromethyl)phenyl.

4. The compound of formula (I) according to claim 1, wherein $R_7$ and $R_8$ represent, independently of each other, a hydrogen atom or a methyl group.

5. The compound of formula (I) according to claim 1, wherein:
A represents a group $C_{1-7}$-alkylene optionally substituted with one or two groups $R_a$;
B represents a group $C_{1-7}$-alkylene optionally substituted with a group $R_b$;
L represents a nitrogen atom substituted with a group $R_c$ or $R_d$;
the carbon atoms of A and of B being optionally substituted with one or more groups $R_f$, which may be identical to or different from each other;
$R_a$ and $R_b$ may together form a bond or a group $C_{1-6}$-alkylene,
$R_a$ and $R_c$ may together form a bond or a group $C_{1-6}$-alkylene;
$R_b$ and $R_c$ may together form a bond or a group $C_{1-6}$-alkylene,
$R_d$ represents a substituent chosen from a group $C_{1-6}$-alkyl, $C_{3-7}$-cycloalkyl, $C_{3-7}$-cycloalkyl-$C_{1-6}$-alkyl, hydroxy-$C_{1-6}$-alkyl, $C_{1-6}$-alkyloxy-$C_{1-6}$-alkyl, $C_{1-6}$-fluoroalkyl or benzyl; and
$R_f$ represents a group $C_{1-6}$-alkyl, hydroxy-$C_{1-6}$-alkyl, $C_{1-6}$-alkyloxy-$C_{1-6}$-alkyl or $C_{1-6}$-fluoroalkyl.

6. The compound of formula (I) according to claim 1, wherein:
the cyclic amine formed by —N-A-L-B— represents a piperazin-1-yl, 3-(R)-methylpiperazin-1-yl, 3,3-dimethylpiperazin-1-yl, cis-3,5-dimethylpiperazin-1-yl, 4-methylpiperazin-1-yl, 4-(2-hydroxyethyl)piperazin-1-yl, 4-(2-fluoroethyl)piperazin-1-yl, 4-isopropylpiperazin-1-yl, 4-cyclopropylpiperazin-1-yl, 4-benzylpiperazin-1-yl, 4-(2-hydroxy-2-methylpropyl)piperazin-1-yl, 4-(3-hydroxy-3-methylbutyl)piperazin-1-yl, (S)-octahydropyrrolo[1,2-a]pyrazin-2-yl, (1S,4S)-2,5-diazabicyclo[2.2.1]hept-2-yl, 5-(2-hydroxyethyl)-(1S,4S)-2,5-diazabicyclo[2.2.1]hept-2-yl, 5-isopropyl-(1S,4S)-2,5-diazabicyclo[2.2.1]hept-2-yl, hexahydropyrrolo[3,4-c]pyrrol-2(1H)-yl, 5-methyl-hexahydropyrrolo[3,4-c]pyrrol-2-(1H)-yl, 5-(2-isopropyl)hexahydropyrrolo[3,4-c]pyrrol-2-(1H)-yl, 5-(2-hydroxyethyl)hexahydropyrrolo[3,4-c]pyrrol-2-(1H)-yl, 5-(benzyl)hexahydro-pyrrolo[3,4-c]pyrrol-2-(1H)-yl, 3-(hydroxymethyl)piperazin-1-yl or 3-fluoromethylpiperazin-1-yl group.

7. The compound of formula (I) according to claim 1, wherein:
A represents a group $C_{1-7}$-alkylene;
B represents a group $C_{1-7}$-alkylene;
L represents a carbon atom substituted with two groups $R_{e2}$;
the carbon atoms of A and of B being optionally substituted with one or more groups $R_f$, which may be identical to or different from each other;
$R_f$ represents a group $C_{1-6}$-alkyl; and
two $R_{e2}$ groups form, with the carbon atom which bears them, an azetidine, pyrrolidine, piperidine or morpholine group.

8. The compound of formula (I) according to claim 1, wherein the cyclic amine formed by N-A-L-B— represents a 2,9-diazaspiro[5.5]undec-3-yl or 1-oxa-4,9-diazaspiro[5.5]undec-9-yl group.

9. The compound of formula (I) according to claim 1, wherein:
A represents a group $C_{1-7}$-alkylene;
B represents a group $C_{1-7}$-alkylene;
L represents a carbon atom substituted with a group $R_{e1}$ and a group $R_d$;
$R_d$ represents a hydrogen atom;
$R_{e1}$ represents a group —$NR_4R_5$ or pyrrolidinyl; and
$R_4$ and $R_5$ represent, independently of each other, a hydrogen atom or a group $C_{1-6}$-alkyl, $C_{3-7}$-cycloalkyl or $C_{3-7}$-cycloalkyl-$C_{1-6}$-alkyl.

10. The compound of formula (I) according to claim 1, wherein:
the cyclic amine formed by —N-A-L-B— represents a (R,S)-3-[pyrrolidin-1-yl]-pyrrolidin-1-yl or 4-(pyrrolidin-1-yl)piperidin-1-yl group.

11. The compound of formula (I) according to claim 1, wherein:
$R_2$ represents a phenyl, 3-fluorophenyl, 4-fluorophenyl, 3,4-difluorophenyl, 3,5-difluorophenyl, 3,5-dichlorophenyl, 3,5-dimethylphenyl or 3,5-di(trifluoromethyl)phenyl group; the cyclic amine formed by —N-A-L-B— represents a piperazin-1-yl, 3-(R)-methylpiperazin-1-yl, 3,3-dimethylpiperazin-1-yl, cis-3,5-dimethylpiperazin-1-yl, 4-methylpiperazin-1-yl, 4-(2-hydroxyethyl)piperazin-1-yl, 4-(2-fluoroethyl)piperazin-1-yl, 4-isopropylpiperazin-1-yl, 4-cyclopropylpiperazin-1-yl, 4-benzylpiperazin-1-yl, 4-(2-hydroxy-2-methylpropyl)piperazin-1-yl, 4-(3-hydroxy-3-methylbutyl)piperazin-1-yl, (S)-octahydropyrrolo[1,2-c]pyrazin-2-yl, (1S,4S)-2,5-diazabicyclo[2.2.1]hept-2-yl, 5-(2-hydroxyethyl)-(1S,4S)-2,5-diazabicyclo[2.2.1]hept-2-yl, 5-isopropyl-(1S,4S)-2,5-diazabicyclo[2.2.1]hept-2-yl, hexahydropyrrolo[3,4-c]pyrrol-2-(1H)-yl, 5-methyl-hexahydropyrrolo[3,4-c]pyrrol-2-(1H)-yl, 5-(2-isopropyl)hexahydropyrrolo-[3,4-c]pyrrol-2-(1H)-yl, 5-(2-hydroxyethyl)hexahydropyrrolo[3,4-c]pyrrol-2-(1H)-yl, 5-(benz-yl)hexahydro-pyrrolo[3,4-c]pyrrol-2-(1H)-yl, 3-(hydroxymethyl)piperazin-1-yl or 3-fluoromethylpiperazin-1-yl group; and
$R_7$ and $R_8$ represent, independently of each other, a hydrogen atom or a methyl group.

12. The compound of formula (I) according to claim 1, wherein:
$R_2$ represents a 4-fluorophenyl, 3,5-difluorophenyl, 3,5-dichlorophenyl, 3,5-dimethylphenyl or 3,5-di(trifluoromethyl)phenyl group;
the cyclic amine formed by —N-A-L-B— represents a (R,S)-3-[pyrrolidin-1-yl]pyrrolidin-1-yl or 4-(pyrrolidin-1-yl)piperidin-1-yl group; and
$R_7$ and $R_8$ represent a hydrogen atom.

13. The compound of formula (I) according to claim 1, which is selected from the group consisting of:
2-(4-fluorophenyl)-6-piperazin-1-yl-3-pyridazin-4-yl-imidazo[1,2-b]pyridazine;
2-(4-fluorophenyl)-6-((R)-3-methylpiperazin-1-yl)-3-pyridazin-4-yl-imidazo[1,2-b]pyridazine;
6-(3,3-dimethylpiperazin-1-yl)-2-(4-fluorophenyl)-3-pyridazin-4-yl-imidazo[1,2-b]pyridazine;
6-(cis-3,5-dimethylpiperazin-1-yl)-2-(4-fluorophenyl)-3-pyridazin-4-yl-imidazo-[1,2-b]pyridazine;
2-(4-fluorophenyl)-6-(4-methylpiperazin-1-yl)-3-pyridazin-4-yl-imidazo[1,2-b]pyridazine;

2-{4-[2-(4-fluorophenyl)-3-pyridazin-4-yl-imidazo[1,2-b]pyridazin-6-yl]piperazin-1-yl}-ethanol;
6-[4-(2-fluoroethyl)piperazin-1-yl]-2-phenyl-3-pyridazin-4-yl-imidazo[1,2-b]pyridazine;
6-[4-(2-fluoroethyl)piperazin-1-yl]-2-(4-fluorophenyl)-3-pyridazin-4-yl-imidazo-[1,2-b]pyridazine;
6-(4-isopropylpiperazin-1-yl)-2-phenyl-3-pyridazin-4-yl-imidazo[1,2-b]pyridazine;
2-(3-fluorophenyl)-6-(4-isopropylpiperazin-1-yl)-3-pyridazin-4-yl-imidazo[1,2-b]pyridazine;
2-(4-fluorophenyl)-6-(4-isopropylpiperazin-1-yl)-3-pyridazin-4-yl-imidazo[1,2-b]pyridazine;
2-(4-fluorophenyl)-6-(4-isopropylpiperazin-1-yl)-7,8-dimethyl-3-pyridazin-4-yl-imidazo-[1,2-b]pyridazine;
2-(3,5-dimethylphenyl)-6-(4-isopropylpiperazin-1-yl)-3-pyridazin-4-yl-imidazo-[1,2-b]pyridazine;
2-(3,4-difluorophenyl)-6-(4-isopropylpiperazin-1-yl)-3-pyridazin-4-yl-imidazo[1,2-b]pyridazine,
2-(3,5-difluorophenyl)-6-(4-isopropylpiperazin-1-yl)-3-pyridazin-4-yl-imidazo[1,2-b]pyridazine;
2-(3,5-dichlorophenyl)-6-(4-isopropylpiperazin-1-yl)-3-pyridazin-4-yl-imidazo[1,2-b]pyridazine;
2-(3,5-di(trifluoromethyl)phenyl)-6-(4-isopropylpiperazin-1-yl)-3-pyridazin-4-yl-imidazo-[1,2-b]pyridazine;
6-(4-cyclopropylpiperazin-1-yl)-2-(4-fluorophenyl)-3-pyridazin-4-yl-imidazo[1,2-b]pyridazine;
6-(4-benzylpiperazin-1-yl)-2-(4-fluorophenyl)-3-pyridazin-4-yl-imidazo[1,2-b]pyridazine;
1-{4-[2-(4-fluorophenyl)-3-pyridazin-4-yl-imidazo[1,2-b]pyridazin-6-yl]piperazin-1-yl}-2-methylpropan-2-ol;
4-{4-[2-(4-fluorophenyl)-3-pyridazin-4-yl-imidazo[1,2-b]pyridazin-6-yl]piperazin-1-yl}-2-methylbutan-2-ol;
2-(4-fluorophenyl)-6-(S)-hexahydropyrrolo[1,2-a]pyrazin-2-yl-3-pyridazin-4-yl-imidazo-[1,2-b]pyridazine;
6-((1S,4S)-2,5-diazabicyclo[2.2.1]kept-2-yl)-2-(4-fluorophenyl)-3-pyridazin-4-yl-imidazo-[1,2-b]pyridazine;
2-{5-[2-(4-fluorophenyl)-3-pyridazin-4-yl-imidazo[1,2-b]pyridazin-6-yl]-(1S,4S)-2,5-diaza-bicyclo[2.2.1]hept-2-yl}-ethanol;
2-(4-fluorophenyl)-6-(5-isopropyl-(1S,4S)-2,5-diazabicyclo[2.2.1]kept-2-yl)-3-pyridazin-4-yl-imidazo[1,2-b]pyridazine;
2-(4-fluorophenyl)-6-hexahydropyrrolo[3,4-c]pyrrol-2-(1H)-yl-3-pyridazin-4-yl-imidazo-[1,2-b]pyridazine;
2-(4-fluorophenyl)-6-(5-methylhexahydropyrrolo[3,4-c]pyrrol-2(1H)-yl)-3-pyridazin-4-yl-imidazo[1,2-b]pyridazine;
2-(4-fluorophenyl)-6-(5-isopropylhexahydropyrrolo[3,4-c]pyrrol-2-(1H)-yl)-3-pyridazin-4-yl-imidazo[1,2-b]pyridazine;
2-{(5-[2-(4-fluorophenyl)-3-pyridazin-4-yl-imidazo[1,2-b]pyridazin-6-yl]-hexahydropyrrolo-[3,4-c]pyrrol-2-(1H)-yl}-ethanol;
2-(4-fluorophenyl)-6-(5-benzylhexahydropyrrolo[3,4-c]pyrrol-2-(1H)-yl)-3-pyridazin-4-yl-imidazo[1,2-b]pyridazine;
9-[2-(4-fluorophenyl)-3-pyridazin-4-yl-imidazo[1,2-b]pyridazin-6-yl]-2,9-diaza-spiro[5.5]undecane;
9-[2-(4-fluorophenyl)-3-pyridazin-4-yl-imidazo[1,2-b]pyridazin-6-yl]-1-oxa-4,9-diaza-spiro[5.5]undecane;
6-[1,3']bipyrrolidinyl-1'-yl-2-(4-fluorophenyl)-3-pyridazin-4-yl-imidazo[1,2-b]pyridazine;
2-(4-fluorophenyl)-3-pyridazin-4-yl-6-(4-pyrrolidin-1-yl-piperidin-1-yl)-imidazo-[1,2-b]pyridazine;
2-(3,5-dimethylphenyl)-3-pyridazin-4-yl-6-(4-pyrrolidin-1-yl-piperidin-1-yl)-imidazo-[1,2-b]pyridazine;
2-(3,5-difluorophenyl)-3-pyridazin-4-yl-6-(4-pyrrolidin-1-yl-piperidin-1-yl)-imidazo-[1,2-b]pyridazine;
2-(3,5-dichlorophenyl)-3-pyridazin-4-yl-6-(4-pyrrolidin-1-yl-piperidin-1-yl)-imidazo-[1,2-b]pyridazine;
2-(3,5-di(trifluoromethyl)phenyl)-3-pyridazin-4-yl-6-(4-pyrrolidin-1-yl-piperidin-1-yl)-imidazo[1,2-b]pyridazine;
(+/−)-{4-[2-(4-fluorophenyl)-3-pyridazin-4-ylimidazo[1,2-b]pyridazin-6-yl]piperazin-2-yl}methanol;
(+/−)-6-(3-fluoromethylpiperazin-1-yl)-2-(4-fluorophenyl)-3-pyridazin-4-ylimidazo-[1,2-b]pyridazine;
6-(5-methylhexahydropyrrolo[3,4-c]pyrrol-2(1H)-yl)-2-phenyl-3-pyridazin-4-ylimidazo-[1,2-b]pyridazine;
2-(3-fluorophenyl)-6-(5-methylhexahydropyrrolo[3,4-c]pyrrol-2(1H)-yl)-3-pyridazin-4-ylimidazo[1,2-b]pyridazine;
2-(4-fluorophenyl)-7-methyl-6-(5-methylhexahydropyrrolo[3,4-c]pyrrol-2-(1H)-yl)-3-pyridazin-4-ylimidazo[1,2-b]pyridazine;
2-(4-fluorophenyl)-8-methyl-6-(5-methylhexahydropyrrolo[3,4-c]pyrrol-2(1H)-yl)-3-pyridazin-4-ylimidazo[1,2-b]pyridazine; and
2-(3,4-difluorophenyl)-6-(5-methylhexahydropyrrolo[3,4-c]pyrrol-2(1H)-yl)-3-pyridazin-4-ylimidazo[1,2-b]pyridazine:

or a pharmaceutically acceptable salt thereof.

14. A pharmaceutical composition comprising a compound of formula (I) according to claim 1 or a pharmaceutically acceptable salt thereof and at least one pharmaceutically acceptable excipient.

15. A pharmaceutical composition comprising a compound of formula (I) according to claim 13 or a pharmaceutically acceptable salt thereof and at least one pharmaceutically acceptable excipient.

* * * * *